US008629280B2

(12) United States Patent
Ackerman et al.

(10) Patent No.: US 8,629,280 B2
(45) Date of Patent: Jan. 14, 2014

(54) METHODS FOR OLIGOMERIZING OLEFINS WITH CHROMIUM PYRIDINE ETHER CATALYSTS

(75) Inventors: Lily J. Ackerman, San Francisco, CA (US); Gary Michael Diamond, Menlo Park, CA (US); Keith Anthony Hall, San Jose, CA (US); James M. Longmire, San Jose, CA (US); Vince J. Murphy, San Jose, CA (US); Dawn E. Verdugo, Kansas City, MO (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 857 days.

(21) Appl. No.: 11/956,133

(22) Filed: Dec. 13, 2007

(65) Prior Publication Data

US 2008/0200743 A1    Aug. 21, 2008

Related U.S. Application Data

(60) Provisional application No. 60/879,131, filed on Jan. 8, 2007.

(51) Int. Cl.
*C07D 213/30* (2006.01)

(52) U.S. Cl.
USPC .......................................... 546/339

(58) Field of Classification Search
USPC ........................... 546/339; 556/57
See application file for complete search history.

(56) References Cited

U.S. PATENT DOCUMENTS

| | | | |
|---|---|---|---|
| 3,333,016 A | 7/1967 | Schultz et al. |
| 3,627,700 A | 12/1971 | Zuech |
| 3,726,939 A | 4/1973 | Zuech |
| 4,668,838 A | 5/1987 | Briggs |
| 5,137,994 A | 8/1992 | Goode et al. |
| 5,198,563 A | 3/1993 | Reagen et al. |
| 5,382,738 A | 1/1995 | Reagen et al. |
| 5,438,027 A | 8/1995 | Reagen et al. |
| 5,439,862 A | 8/1995 | Kemp |
| 5,491,272 A | 2/1996 | Tanaka et al. |
| 5,523,507 A | 6/1996 | Reagen et al. |
| 5,543,375 A | 8/1996 | Lashier et al. |
| 5,637,660 A | 6/1997 | Nagy et al. |
| 5,744,677 A | 4/1998 | Wu |
| 5,750,816 A | 5/1998 | Araki et al. |
| 5,750,817 A | 5/1998 | Tanaka et al. |
| 5,856,257 A | 1/1999 | Freeman et al. |
| 5,856,612 A | 1/1999 | Araki et al. |
| 5,910,619 A | 6/1999 | Urata et al. |
| 5,968,866 A | 10/1999 | Wu |
| 6,103,657 A | 8/2000 | Murray |
| 6,133,495 A | 10/2000 | Urata et al. |
| 6,320,005 B1 | 11/2001 | Murray |
| 6,344,594 B1 | 2/2002 | Sen et al. |
| 6,706,829 B2 | 3/2004 | Boussie et al. |
| 6,713,577 B2 | 3/2004 | Boussie et al. |
| 6,727,361 B2 | 4/2004 | LaPointe et al. |
| 6,750,345 B2 | 6/2004 | Boussie et al. |
| 6,828,397 B2 | 12/2004 | Boussie et al. |
| 7,256,296 B2 | 8/2007 | Diamond et al. |
| 2002/0035029 A1 | 3/2002 | Yoshida et al. |
| 2004/0087434 A1 | 5/2004 | Llatas et al. |
| 2005/0113622 A1 | 5/2005 | Drent et al. |
| 2006/0094839 A1 | 5/2006 | Diamond et al. |
| 2006/0247399 A1 | 11/2006 | McConville et al. |
| 2006/0247483 A1 | 11/2006 | McConville et al. |
| 2007/0185362 A1 | 8/2007 | Lattner et al. |

FOREIGN PATENT DOCUMENTS

| | | |
|---|---|---|
| CA | 2087578 | 7/1994 |
| CA | 2115639 | 9/1994 |
| EP | 0537609 | 8/1996 |
| EP | 0416304 | 3/1997 |
| EP | 0614865 | 10/1997 |
| EP | 0699648 | 4/1998 |
| EP | 0780353 | 8/2000 |
| EP | 0608447 | 10/2001 |
| EP | 1 325 924 | 7/2003 |
| EP | 1110930 | 9/2003 |
| EP | 1 325 924 | 12/2003 |
| EP | 1 367 069 | 12/2003 |
| JP | 2000-169513 | 6/2000 |
| JP | 2001187345 | 7/2001 |
| WO | WO 00/69923 | 11/2000 |
| WO | WO 01/68572 | 9/2001 |
| WO | WO 02/04119 | 1/2002 |
| WO | WO 02/066404 | 8/2002 |
| WO | WO 02/083306 | 10/2002 |
| WO | WO 03/004158 | 1/2003 |
| WO | WO 03/053890 | 7/2003 |
| WO | WO 03/054038 | 7/2003 |

(Continued)

OTHER PUBLICATIONS

Pincus et. al, "Selective fluorescence detection of divalent and trivalent metal ions with functionalized lipid membranes." Journal of Materials Chemistry, 2005, 15(27-28), 2938-2945.*
Antonietti et. al. "Synthesis of metal-complexing latexes via polymerization in microemulsion." Macromolecular Rapid Communications, 1995, 16(4), 283-9.*
Okada et. al. "Synthesis of a new calix[4]arene family using syn-dihydroxy[2.n]metacyclophane as a building block." Synlett 1995, 85-9.*
Nabeshima et. al. "Selective Recognition for Heavy and' Transition Metals by Novel Polyethers Bearing Bipyridines, and Molecular Chiralky of Pseudocrown Structure in the Cu(I) Complex" Tetrahedron Letters 1990, 31 (45), 6543-6546.*
"[Bis(2-methyl-1-pyridyl)phenylphosphine-kappa.2N,P,N']trichlorochromium(I II) acetonitrile solvate", Klausmeyer et al., *Acta Crystallographica*, Section E: Structure Reports Online, E62(10), M2415-M2416.

(Continued)

*Primary Examiner* — David K O Dell

(57) ABSTRACT

The present invention provides a method of producing oligomers of olefins, comprising reacting olefins with a catalyst under oligomerization conditions. The catalyst can be the product of the combination of a chromium compound and a pyridyl ether compound. In particular embodiments, the catalyst compound can be used to trimerize or tetramerize ethylene to 1-hexene, 1-octene, or mixtures of 1-hexene and 1-octene.

27 Claims, 1 Drawing Sheet

(56) References Cited

FOREIGN PATENT DOCUMENTS

| WO | WO 2004/056477 | 7/2004 |
|---|---|---|
| WO | WO 2004/056478 | 7/2004 |
| WO | WO 2004/056479 | 7/2004 |
| WO | WO 2004/056480 | 7/2004 |
| WO | WO 2006/096881 | 9/2006 |

OTHER PUBLICATIONS

"Chromium(II) and Chromium(III) Complexes Supported by Tris(2-pyridylmethyl)amine: Synthesis, Structures, and Reactivity", Robertson et al., *Inorg. Chem.* 42, pp. 6875-6885 (2003).

"First Cr(III)-SNS Complexes and Their Use as Highly Efficient Catalysts for the Trimerization of Ethylene to 1-Hexane," McGuinness et al., *J. Am. Chem. Soc.* 125, 5272-5273 (2003).

"High activity ethylene trimerisation catalysts based on diphosphine ligands," Carter et al., *Chem. Commun.*, 2002, pp. 858-859.

"New planar chiral P,N-ligands containing tricarbonyl(arene)chromium for enantioselective asymmetric hydroboration of styrenes", Son et al., *Tetrahedron: Asymmerty* 10 (1999) pp. 347-354.

"New Tantalum-Based Catalyst System for the Selective Trimerization of Ethene to 1-Hexane," Andes et al., *J. Am. Chem. Soc.* 123, 7423-7424 (2001).

"Novel basic ligands for the homogeneous catalytic homologation of methanol to ethanol. I. Synthesis of basic tridentate phosphorus-nitrogen containing chelate ligands and their behavior towards carbonyl compounds of Group VI metals", Lindner et al., *Anorganische Chemie, Organische Chemie*, 38B(4), pp. 417-425.

"Sulfur ligand metal complexes, Part 10, Sulfur-nitrogen donor ligand complexes of the Group VI metal carbonyls", Ainscough et al., *Inorganica Chimica Acta*, 50(2), pp. 215-220.

"Synthetic and Structural Studies of the Coordination Behaviour of 2-Pyridylbis(diphenylphosphino)methane", Mague et al., *Inorganic Chemistry*, 40(8), pp. 1962-1971.

"Synthesis and use in palladium-catalyzed asymmetric allylic alkylation of new planar chiral chromium complexes of 1,2-disubstituted areness having pyridine and aryl phosphine groups", Han et al., *Tetrahedron: Asymmetry* 10 (1999) pp. 2853-2861.

"Synthesis and characterization of some novel mixed-ligand cyanonitrosyl {CrNO} 5 heterocomplexes of chromium(I) with potentially tridentate benzothiazole derivatives", Maurya et al., *Synthesis and Reactivity in Inorganic and Metal-Organic Chemistry*, 22(8) pp. 1227-1237.

Esteruelas, et al., "Synthesis, X-Ray structure, and polymerization activity of a bis(oxazolinyl)pyridine chromium(III) complex," *New Journal of Chemistry* (2002), vol. 26, No. 11, pp. 1542-1544.

Gibson et al., "Advances in Non-Metallocene Olefin Polymerization Catalysis", Gibson & Spitzmesser, *Chem. Rev.*, 2003, vol. 103, No. 1, pp. 283-315.

Olivier-Bourbigou et al., "Dimerization and Codimerization", *Applied Homogeneous Catalysis with Organometallic Compounds* (2nd Edition), 2002, vol. 1, pp. 253-265, Ed. Cornils, B., & Herrmann, W. A., Wiley-VCH Verlag GmbH, Weinheim, Germany.

Small et al., "New Chromium Complexes for Ethylene Oligomerization: Extended Use of Tridentate Ligands in Metal-Catalyzed Olefin Polymerization", *Macromolecules* 2004, vol. 37, pp. 4375-4386.

Zuech, E. A., "Polymerizations with homogeneous chromium catalysts", *J. of Polym. Sci., Polym. Chem. Ed.*, 1972, vol. 10, No. 12, pp. 3665-3672.

Britovsek et al., "The Search for New-Generation Olefin Polymerization Catalysts: Life beyond Metallocenes", *Angewandte Chem. Int. Ed.*, 1999, vol. 38, No. 4, pp. 428-447.

Britovsek, G. et al., "*The Search for New-Generation Olefin Polymerization Catalysts: Life beyond Metallocenes*", Angew. Chem. Int. Ed., 1999, vol. 38, pp. 428-447.

Gibson, V. et al., "*Advances in Non-Metallocene Olefin Polymerization Catalysis*", Chemical Review, 2003, vol. 103, No. 1, pp. 283-315.

Oliver-Bourbigou, H. et al., "*Dimerization and Codimerization*", Applied Homogeneous Catalysis with Organometallic Compounds, 2002, pp. 253-265.

Small, B.L. et al., "*New Chromium Complexes for Ethylene Oligomerization: Extended Use of Tridentate Ligands in Metal-Catalyzed Olefin Polymerization*", Macromolecules, 2004, vol. 37, No. 12, pp. 4375-4386.

Zuech, E.A., "*Polymerizations with Homogeneous Chromium Catalysts*", Journal of Polymer Science, Polymer Chemical Edition, 1972, vol. 10, pp. 3665-3672.

\* cited by examiner

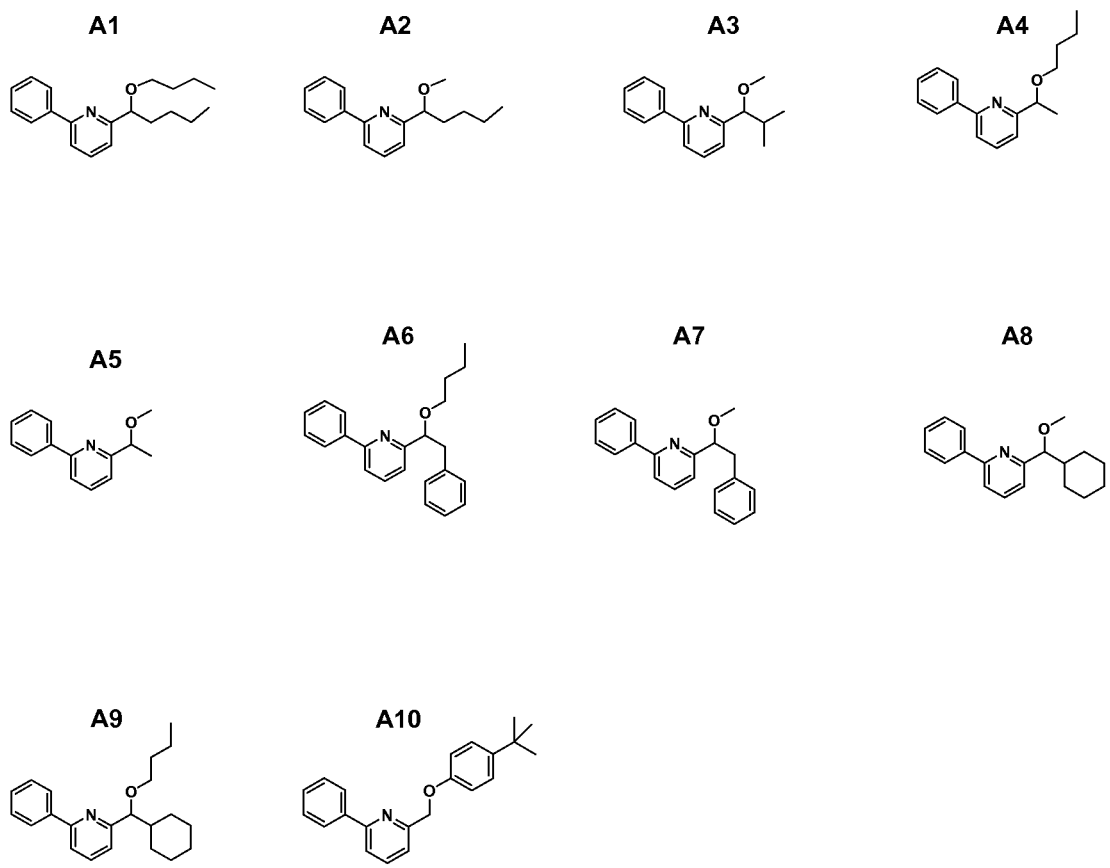

METHODS FOR OLIGOMERIZING OLEFINS WITH CHROMIUM PYRIDINE ETHER CATALYSTS

PRIORITY CLAIM

This application claims priority to and the benefit of U.S. Ser. No. 60/879,131, filed Jan. 8, 2007.

STATEMENT OF RELATED CASES

This application is related to concurrently filed patent applications U.S. Ser. No. 60/879,128, filed Jan. 8, 2007, U.S. Ser. No. 60/879,127, filed Jan. 8, 2007, U.S. Ser. No. 60/879,129, filed Jan. 8, 2007, and U.S. Ser. No. 60/879,130, filed Jan. 8, 2007.

FIELD OF THE INVENTION

This invention relates to the selective oligomerization (specifically trimerization and/or tetramerization) of olefins (specifically ethylene) using chromium based catalysts.

BACKGROUND OF THE INVENTION

The oligomerization of ethylene typically returns a broad distribution of 1-olefins having an even number of carbon atoms ($C_4$, $C_6$, $C_8$, $C_{10}$, etc.). These products range in commercial value, of which 1-hexene may be the most useful, as it is a comonomer commonly used in the production of commercial ethylene based copolymers.

Several catalysts useful for the oligomerization of olefin monomers have also been developed, including the trimerization of ethylene. Several of these catalysts use chromium as a metal center. For example, U.S. Pat. No. 4,668,838, assigned to Union Carbide Chemicals and Plastics Technology Corporation, discloses a chromium catalyst complex formed by contacting a chromium compound with hydrolyzed hydrocarbyl aluminum and a donor ligand such as hydrocarbyl isonitriles, amines, and ethers. U.S. Pat. No. 5,137,994 discloses a chromium catalyst formed by the reaction products of bis-triarylsilyl chromates and trihydrocarbylaluminum compounds.

U.S. Pat. No. 5,198,563 and related patents, issued to Philips Petroleum Company, disclose chromium-containing catalysts containing monodentate amine/amide ligands. A chromium catalyst complex formed by contacting an aluminum alkyl or a halogenated aluminum alkyl and a pyrrole-containing compound prior to contacting with a chromium containing compound is disclosed in U.S. Pat. Nos. 5,382,738, 5,438,027, 5,523,507, 5,543,375, and 5,856,257. Similar catalyst complexes are also disclosed in EP0416304B1, EP0608447B1, EP0780353B1, and CA2087578.

Several patents assigned to Mitsubishi Chemicals also disclose chromium catalyst complexes formed from a chromium compound, a pyrrole ring-containing compound, an aluminum alkyl, and a halide containing compound, including U.S. Pat. Nos. 5,491,272, 5,750,817, and 6,133,495. Other catalyst complexes are formed by contacting a chromium compound with a nitrogen containing compound such as a primary or secondary amine, amide, or imide, and an aluminum alkyl, as disclosed in U.S. Pat. Nos. 5,750,816, 5,856,612, and 5,910,619.

EP0537609 discloses a chromium complex containing a coordinating polydentate ligand and an alumoxane. Similarly, CA2115639 discloses a polydentate ligand.

EP0614865B1, issued to Sumitomo Chemical Co., Ltd., discloses a catalyst prepared by dissolving a chromium compound, a heterocyclic compound having a pyrrole ring or an imidazole ring, and an aluminum compound. EP0699648B1 discloses a catalyst obtained by contacting chromium containing compound with a di- or tri-alkyl aluminum hydride, a pyrrole compound or a derivative thereof, and a group 13 (III B) halogen compound.

WO03/053890, and McGuinness et al., *J. Am. Chem. Soc.* 125, 5272-5273, (2003), disclose a chromium complex of tridentate ligands and methylalumoxane (MAO) cocatalyst. However, due to serious drawbacks in the preparation of the—containing system, the use of a thioether donor group to replace the phosphorus donor in the ligands was also investigated.

WO02/083306A2 discloses a catalyst formed from a chromium source, a substituted phenol, and an organoaluminum compound. WO03/004158A2 discloses a catalyst system which includes a chromium source and a ligand comprising a substituted five membered carbocyclic ring or similar derivatives.

U.S. Pat. No. 5,968,866 discloses a catalyst comprising a chromium complex which contains a coordinating asymmetric tridentate phosphine, arsine, or stibane ligand (hydrocarbyl groups) and an alumoxane. Carter et al., *Chem. Commun.*, 2002, pp. 858-859 disclosed an ethylene trimerization catalyst obtained by contacting a chromium source, ligands bearing ortho-methoxy-substituted aryl groups, and an alkyl alumoxane activator. Similarly, WO02/04119A1 discloses a catalyst comprising a source of chromium, molybdenum, or tungsten, and a ligand containing at least one phosphorus, arsenic, or antimony atom bound to at least one (hetero) hydrocarbyl group.

Japanese patent application JP 2001187345A2 (Tosoh Corp., Japan) discloses ethylene trimerization catalysts comprising chromium complexes having tris(pyrazol-1-yl)methane ligands.

US 2005/0113622 (equivalent to WO 2005/039758) discloses Cr based trimerization catalysts.

Additional catalysts useful for oligomerizing olefins include those disclosed in U.S. Ser. No. 11/371,614; filed Mar. 9, 2006; U.S. Ser. No. 11/371,983, filed Mar. 9, 2006; and U.S. Ser. No. 60/841,226, filed Aug. 30, 2006.

Other pertinent references include *J. Am. Chem. Soc.* 123, 7423-7424 (2001), WO01/68572A1, WO02/066404A1, WO04/056477, WO04/056478, WO04/056479, WO04/056480, EP1110930A1, U.S. Pat. Nos. 3,333,016, 5,439,862, 5,744,677, and 6,344,594 and U.S. Pat. App. Pub. No. 2002/0035029A1.

Although each of the above described catalysts is useful for the trimerization of ethylene, there remains a desire to improve the performance of olefin oligomerization catalysts from the standpoint of productivity and selectivity for oligomers such as 1-hexene or 1-octene.

Several pyridyl amine catalyst complexes have been disclosed for the polymerization or copolymerization of ethylene, propylene, isobutylene, octene, and styrene by Symyx Technologies, Inc. in U.S. Pat. Nos. 6,713,577, 6,750,345, 6,706,829, 6,727,361, and 6,828,397. Pyridyl amines were also disclosed in U.S. Pat. Nos. 6,103,657 and 6,320,005, assigned to Union Carbide Chemical and Plastics Technology Corporation, in which zirconium was used as the metal center, and the catalyst complex was used to polymerize alpha-olefins, and in U.S. Pat. No. 5,637,660, assigned to Lyondell Petrochemical Company, which also describes Group 4 complexes of pyridyl amine ligands. Robertson et al., *Inorg.*

Chem. 42, pp 6875-6885 (2003), discloses chromium complexes of tris(2-pyridylmethyl)amine for ethylene polymerization.

This invention also relates to U.S. patent application Ser. Nos. 60/611,943, 11/232,982 and 11/233,227 and WO2006096881 A1.

What is needed is a catalyst system that can be readily prepared and that selectively oligomerizes ethylene or other olefins with both high activity and high selectivity.

SUMMARY OF THE INVENTION

The present invention provides methods and compositions to produce oligomers of olefins, comprising reacting olefins with a catalyst system under oligomerization conditions. The oligomerization reaction can have a selectivity of at least 70 mole percent for the desired oligomer. Typically the catalyst system is formed from the combination of:

(1) a ligand characterized by the following general formula:

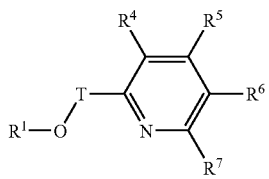

wherein $R^1$ is selected from the group consisting of optionally substituted hydrocarbyl and heteroatom containing hydrocarbyl;

T is a bridging group of the general formula $-(T'R^2R^3)-$, where T' is carbon or silicon, $R^2$ and $R^3$ are independently selected from the group consisting of hydrogen, halogen, and optionally substituted hydrocarbyl, heteroatom containing hydrocarbyl, silyl, boryl, and combinations thereof, provided that $R^2$ and $R^3$ groups may be joined together to form one or more optionally substituted ring systems having from 3-50 non-hydrogen atoms (e.g., cyclopropyl, where T'=C, and $R^2$ and $R^3$ together form $-CH_2-CH_2-$; or cyclohexyl, where T'=C and $R^2$ and $R^3$ groups together form $-CH_2-CH_2-CH_2-CH_2-$);

$R^4$, $R^5$, $R^6$ and $R^7$ are independently selected from the group consisting of hydrogen, halogen, nitro, and optionally substituted hydrocarbyl and heteroatom containing hydrocarbyl, alkoxy, aryloxy, silyl, boryl, phosphino, amino, alkylthio, arylthio, and combinations thereof, and optionally two or more $R^1$, $R^2$, $R^3$, $R^4$, $R^5$, $R^6$ and $R^7$ groups may be joined to form one or more optionally substituted ring systems;

(2) a metal precursor compound characterized by the general formula $Cr(L)_n$ where each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, wherein two or more L groups may be combined in a ring structure having from 3 to 50 non-hydrogen atoms; n is 1, 2, 3, 4, 5, or 6; and (3) optionally, one or more activators.

The activator used in the method of the present invention can be selected from the group consisting of modified methylalumoxane (MMAO), methylalumoxane (MAO), trimethylaluminum (TMA), triisobutyl aluminum (TIBA), polymethylalumoxane-IP (PMAO-IP), N,N-di(n-decyl)-4-n-butyl-anilinium tetrakis(perfluorophenyl)borate, and mixtures thereof.

The metal precursor used in the method of the present invention can be selected from the group consisting of $(THF)_3CrMeCl_2$, $(THF)_3CrCl_3$, $(Mes)_3Cr(THF)$, $[\{TFA\}_2Cr(OEt_2)]_2$, $(THF)_3CrPh_3$, $(THF)_3Cr(q\ 2\text{-}2,2'\text{-Biphenyl})Br$ and mixtures thereof.

The method of the present invention can oligomerize, e.g. trimerize or tetramerize, $C_2$ to $C_{12}$ olefins. In one embodiment of the present invention, the olefin can be ethylene. The oligomerization or ethylene can produce 1-hexene, 1-octene, or mixtures thereof. The reaction in the method of the present invention can occur in a hydrocarbon solvent.

Further aspects of this invention will be evident to those of skill in the art upon review of this specification.

BRIEF DESCRIPTION OF THE DRAWINGS

FIG. 1 illustrates pyridyl-ether ligands according to embodiments of the invention.

DETAILED DESCRIPTION

The inventions disclosed herein include chromium metal complexes and compositions, which are useful as catalysts for the selective oligomerization of olefins, specifically C2 to C12 olefins and especially C2 to C8 olefins, including the trimerization and/or tetramerization of ethylene.

For the purposes of this invention and the claims thereto when an oligomeric material (such as a dimer, trimer, or tetramer) is referred to as comprising an olefin, the olefin present in the material is the reacted form of the olefin. Likewise, the active species in a catalytic cycle may comprise the neutral or ionic forms of the catalyst. In addition, a reactor is any container(s) in which a chemical reaction occurs.

As used herein, the new numbering scheme for the Periodic Table Groups is used as set out in CHEMICAL AND ENGINEERING NEWS, 63(5), 27 (1985).

As used herein, the phrase "characterized by the formula" is not intended to be limiting and is used in the same way that "comprising" is commonly used. The term "independently selected" is used herein to indicate that the groups in question—e.g., $R_1$, $R_2$, $R_3$, $R_4$, and $R_5$— can be identical or different (e.g., $R_1$, $R_2$, $R_3$, $R_4$, and $R_5$ may all be substituted alkyls, or $R_1$ and $R_2$ may be a substituted alkyl and $R_3$ may be an aryl, etc.). Use of the singular includes use of the plural and vice versa (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. In addition, the term "catalyst" will be understood by those of skill in the art to include either activated or unactivated forms of the molecules the comprise the catalyst, for example, a procatalyst and including complexes and activators or compositions of ligands, metal precursors and activators and optionally including scavengers and the like. For purposes of this invention, a catalyst system is defined to be the combination of an activator and a metal ligand complex or the combination of an activator, a ligand and a metal precursor. A metal ligand complex is defined to be the product of the combination of a metal precursor and a ligand. For the purposes of illustration, representative certain groups are defined herein. These definitions are intended to supplement and illustrate, not preclude, the definitions known to those of skill in the art.

"Optional" or "optionally" means that the subsequently described event or circumstance may or may not occur, and that the description includes instances where the event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "substituted" as in "substituted hydrocarbyl," "substituted aryl," "substituted alkyl," and the like, means that in the group in question (i.e., the hydrocarbyl, alkyl, aryl or other moiety that follows the term), at least one hydrogen atom bound to a carbon atom is replaced with one or more substituent groups such as hydroxy, alkoxy, alkylthio, phosphino, amino, halo, silyl, and the like. When the term "substituted" introduces a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

The term "saturated" refers to the lack of double and triple bonds between atoms of a radical group such as ethyl, cyclohexyl, pyrrolidinyl, and the like. The term "unsaturated" refers to the presence of one or more double and triple bonds between atoms of a radical group such as vinyl, allyl, acetylide, oxazolinyl, cyclohexenyl, acetyl and the like, and specifically includes alkenyl and alkynyl groups, as well as groups in which double bonds are delocalized, as in aryl and heteroaryl groups as defined below.

The terms "cyclo" and "cyclic" are used herein to refer to saturated or unsaturated radicals containing a single ring or multiple condensed rings. Suitable cyclic moieties include, for example, cyclopentyl, cyclohexyl, cyclooctenyl, bicyclooctyl, phenyl, naphthyl, pyrrolyl, furyl, thiophenyl, imidazolyl, and the like. In particular embodiments, cyclic moieties include between 3 and 200 atoms other than hydrogen, between 3 and 50 atoms other than hydrogen or between 3 and 20 atoms other than hydrogen.

The term "hydrocarbyl" as used herein refers to hydrocarbyl radicals containing 1 to about 50 carbon atoms, specifically 1 to about 24 carbon atoms, most specifically 1 to about 16 carbon atoms, including branched or unbranched, cyclic or acyclic, saturated or unsaturated species, such as alkyl groups, alkenyl groups, aryl groups, and the like.

The term "alkyl" as used herein refers to a branched or unbranched saturated hydrocarbon group typically although not necessarily containing 1 to about 50 carbon atoms, such as methyl, ethyl, n-propyl, isopropyl, n-butyl, isobutyl, sec-butyl, t-butyl, octyl, decyl, and the like, as well as cycloalkyl groups such as cyclopentyl, cyclohexyl and the like. Generally, although again not necessarily, alkyl groups herein may contain 1 to about 20 carbon atoms.

The term "alkenyl" as used herein refers to a branched or unbranched, cyclic or acyclic hydrocarbon group typically, although not necessarily, containing 2 to about 50 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 20 carbon atoms.

The term "alkynyl" as used herein refers to a branched or unbranched, cyclic or acyclic hydrocarbon group typically although not necessarily containing 2 to about 50 carbon atoms and at least one triple bond, such as ethynyl, n-propynyl, isopropynyl, n-butynyl, isobutynyl, octynyl, decynyl, and the like. Generally, although again not necessarily, alkynyl groups herein may have 2 to about 20 carbon atoms.

The term "aromatic" is used in its usual sense, including unsaturation that is essentially delocalized across several bonds around a ring. The term "aryl" as used herein refers to a group containing an aromatic ring. Aryl groups herein include groups containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, or phenanthrenyl. In particular embodiments, aryl substituents include 1 to about 200 atoms other than hydrogen, typically 1 to about 50 atoms other than hydrogen, and specifically 1 to about 20 atoms other than hydrogen. In some embodiments herein, multi-ring moieties are substituents and in such embodiments the multi-ring moiety can be attached at an appropriate atom. For example, "naphthyl" can be 1-naphthyl or 2-naphthyl; "anthracenyl" can be 1-anthracenyl, 2-anthracenyl or 9-anthracenyl; and "phenanthrenyl" can be 1-phenanthrenyl, 2-phenanthrenyl, 3-phenanthrenyl, 4-phenanthrenyl, or 9-phenanthrenyl.

The term "alkoxy" as used herein intends an alkyl group bound through a single, terminal ether linkage; that is, an "alkoxy" group may be represented as —O-alkyl where alkyl is as defined above. The term "aryloxy" is used in a similar fashion, and may be represented as —O-aryl, with aryl as defined below. The term "hydroxy" refers to —OH.

Similarly, the term "alkylthio" as used herein intends an alkyl group bound through a single, terminal thioether linkage; that is, an "alkylthio" group may be represented as —S-alkyl where alkyl is as defined above. The term "arylthio" is used similarly, and may be represented as —S-aryl, with aryl as defined below. The term "mercapto" refers to —SH.

The terms "halo" and "halogen" are used in the conventional sense to refer to a chloro, bromo, fluoro or iodo radical.

The terms "heterocycle" and "heterocyclic" refer to a cyclic radical, including ring-fused systems, including heteroaryl groups as defined below, in which one or more carbon atoms in a ring is replaced with a heteroatom—that is, an atom other than carbon, such as nitrogen, oxygen, sulfur, phosphorus, boron or silicon. Heterocycles and heterocyclic groups include saturated and unsaturated moieties, including heteroaryl groups as defined below. Specific examples of heterocycles include pyridine, pyrrolidine, pyrroline, furan, tetrahydrofuran, thiophene, imidazole, oxazole, thiazole, indole, and the like, including any isomers of these. Additional heterocycles are described, for example, in Alan R. Katritzky, *Handbook of Heterocyclic Chemistry*, Pergammon Press, 1985, and in *Comprehensive Heterocyclic Chemistry*, A. R. Katritzky et al., eds., Elsevier, 2d. ed., 1996. The term "metallocycle" refers to a heterocycle in which one or more of the heteroatoms in the ring or rings is a metal.

The term "heteroaryl" refers to an aryl radical that includes one or more heteroatoms in the aromatic ring. Specific heteroaryl groups include groups containing heteroaromatic rings such as thiophene, pyridine, pyrazine, isoxazole, pyrazole, pyrrole, furan, thiazole, oxazole, imidazole, isothiazole, oxadiazole, triazole, and benzo-fused analogues of these rings, such as indole, carbazole, benzofuran, benzothiophene and the like.

More generally, the modifiers "hetero" and "heteroatom-containing", as in "heteroalkyl" or "heteroatom-containing hydrocarbyl group" refer to a molecule or molecular fragment in which one or more carbon atoms is replaced with a heteroatom. Thus, for example, the term "heteroalkyl" refers to an alkyl substituent that is heteroatom-containing. When the term "heteroatom-containing" introduces a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

By "divalent" as in "divalent hydrocarbyl", "divalent alkyl", "divalent aryl" and the like, is meant that the hydrocarbyl, alkyl, aryl or other moiety is bonded at two points to atoms, molecules or moieties with the two bonding points being covalent bonds.

As used herein the term "silyl" refers to the $—SiZ^1Z^2Z^3$ radical, where each of $Z^1$, $Z^2$, and $Z^3$ is independently selected from the group consisting of hydrogen and optionally substituted alkyl, alkenyl, alkynyl, heteroatom-containing alkyl, heteroatom-containing alkenyl, heteroatom-containing alkynyl, aryl, heteroaryl, alkoxy, aryloxy, amino, silyl and combinations thereof.

As used herein the term "boryl" refers to the $—BZ^1Z^2$ group, where each of $Z^1$ and $Z^2$ is as defined above. As used herein, the term "phosphino" refers to the group $—PZ^1Z^2$, where each of $Z^1$ and $Z^2$ is as defined above. As used herein, the term "phosphine" refers to the group: $PZ^1Z^2Z^3$, where each of $Z^1$, $Z^3$ and $Z^2$ is as defined above. The term "amino" is used herein to refer to the group $—NZ^1Z^2$, where each of $Z^1$ and $Z^2$ is as defined above. The term "amine" is used herein to refer to the group: $NZ^1Z^2Z^3$, where each of $Z^1$, $Z^2$ and $Z^3$ is as defined above.

Throughout the text, several abbreviations may be used to refer to specific compounds or elements. Abbreviations for atoms are as given in the periodic table (Li=lithium, for example). Other abbreviations that may be used are as follows: "i-Pr" to refer to isopropyl; "t-Bu" to refer to tertiary-butyl; "i-Bu" to refer to isobutyl; "Me" to refer to methyl; "Et" to refer to ethyl; "Ph" to refer to phenyl; "Mes" to refer to mesityl (2,4,6-trimethyl phenyl); "TFA" to refer to trifluoroacetate; "THF" to refer to tetrahydrofuran; "TsOH" to refer to para-toluenesulfonic acid; "cat." to refer to catalytic amount of; "LDA" to refer to lithium diisopropylamide; "DMF" to refer to dimethylformamide; "eq." to refer to molar equivalents; "TMA" to refer to AlMe$_3$; "TIBA" to refer to Al(i-Bu)$_3$. SJ2BF$_{20}$ refers to [(n-C$_{10}$H$_{21}$)$_2$(4-n-C$_4$H$_9$—C$_6$H$_4$)NH][B(C$_6$F$_5$)$_4$].

This invention relates to methods for selectively oligomerizing (e.g., trimerizing and/or tetramerizing) C$_2$ to C$_{12}$ olefins, specifically ethylene, comprising reacting a catalytic composition or compound(s), optionally with one or more activators, with the olefin. As referred to herein, selective oligomerization refers to producing the desired oligomer with a selectivity of the reaction being at least 70 mol %, more specifically at least 80 mol % of oligomer, with the possibility that an acceptable amount of polymer is present, but with the preference that no polymer is present in the product. In other embodiments, less than 20 weight % of polymer is present, specifically less than 5 weight %, more specifically less than 2 weight %, based upon the total weight of monomer converted to oligomers and polymers, where a polymer is defined to mean a molecule comprising more than 100 mers. In other embodiments, selective oligomerization refers to producing two desired oligomers, with the selectivity of the two desired oligomers summing to at least 80% by sum of the mole % of the desired oligomers.

In another embodiment, this invention relates to a method to trimerize or tetramerize a C$_2$ to C$_{12}$ olefin wherein the method produces at least 70% selectivity for the desired oligomer(s) (specifically at least 80%, specifically at least 85%, specifically at least 90%, specifically at least 95%, specifically at least 98%, specifically at least 99%, specifically 100%), calculated based upon the amount (mol %) of the desired oligomer produced relative to the total yield of product(s); and at least 70% of the olefin monomer reacts to form product (specifically at least 80%, specifically at least 85%, specifically at least 90%, specifically at least 95%, specifically at least 98%, specifically at least 99%, specifically 100%).

This invention also relates to novel metal ligand complexes and or novel combinations of specific ligands disclosed herein and metal precursors.

The methods of this invention specifically refer to contacting the desired monomers with a metal ligand complex or a combination of a ligand and a metal precursor (and optional activators) to form the desired oligomer. Preferred ligands useful in the present invention may be characterized by the general formula:

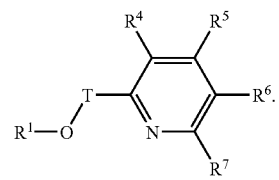

wherein R$^1$ is selected from the group consisting of optionally substituted hydrocarbyl and heteroatom containing hydrocarbyl;

T is a bridging group of the general formula -(T'R$^2$R$^3$)—, where T' is selected from the group consisting of carbon and silicon, R$^2$ and R$^3$ are independently selected from the group consisting of hydrogen, halogen, and optionally substituted hydrocarbyl, heteroatom containing hydrocarbyl, silyl, boryl, and combinations thereof, provided that R$^2$ and R$^3$ groups may be joined together to form one or more optionally substituted ring systems having from 3-50 non-hydrogen atoms. (e.g., cyclopropyl, where T'=C and R$^2$ and R$^3$ together form —CH$_2$—CH$_2$—; or cyclohexyl, where T'=C and R$^2$ and R$^3$ groups together form —CH$_2$—CH$_2$—CH$_2$—CH$_2$—CH$_2$—);

R$^4$, R$^5$, R$^6$ and R$^7$ are independently selected from the group consisting of hydrogen, halogen, nitro, and optionally substituted hydrocarbyl and heteroatom containing hydrocarbyl, alkoxy, aryloxy, silyl, boryl, phosphino, amino, alkylthio, arylthio, and combinations thereof, and optionally two or more R$^1$, R$^2$, R$^3$, R$^4$, R$^5$, R$^6$ and R$^7$ groups may be joined to form one or more optionally substituted ring systems.

Throughout this specification, the presence of one solid line and one dashed line between any pair of atoms is intended to indicate that the bond in question may be a single bond or a double bond, or a bond with bond order intermediate between single and double, such as the delocalized bonding in an aromatic ring.

The detailed synthesis of certain types of heterocycle-ether ligands are specifically discussed below, including pyridyl-ether ligands. Those of ordinary skill in the art will be able to synthesize other embodiments.

The pyridyl-ether ligands in this embodiment can be prepared according to the procedures known to those of ordinary skill in the art, for example, as illustrated by the reaction scheme given in Scheme 1 where $R^1$, $R^2$, $R^3$, $R^4$, $R^5$, $R^6$ and $R^7$, are as defined above.

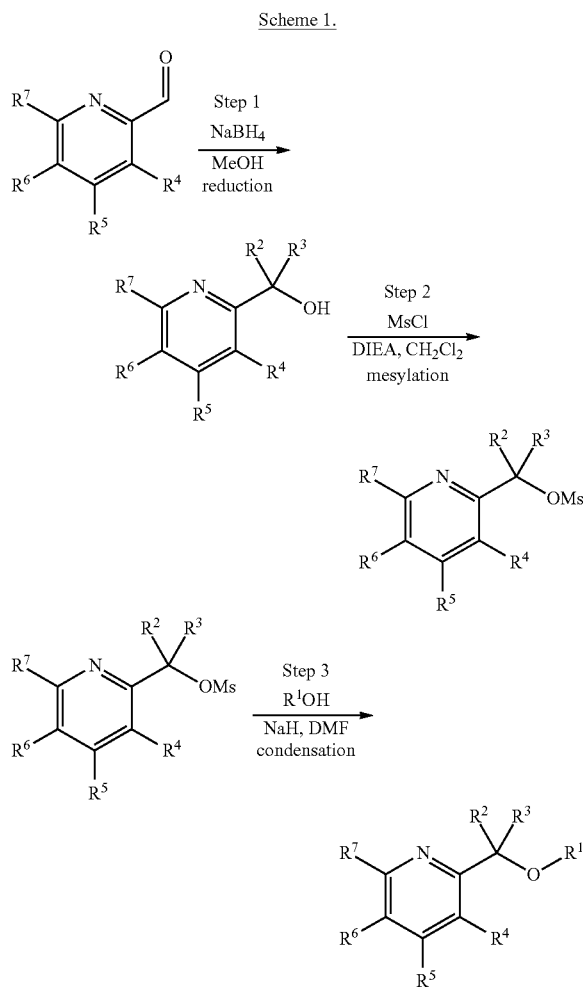

The reaction to produce a pyridine ether ligand where $R^2$ and $R^3$ is hydrogen, while $R^1$ is an optionally substituted alkyl, aryl, or heteroaryl group can be performed in three general reaction steps. In step 1, a pyridine aldehyde can be reacted with sodium borohydride ($NaBH_4$) and methanol in a reduction reaction, replacing the aldehyde group with a primary alcohol group. In step 2, the pyridine alcohol can then be reacted with methansulfonyl chloride (MsCl) and diisopropylethylamine (DIEA) in methylene chloride to produce the mesylated pyridine derivative. The third reaction step installs the $R^1$ group through a displacement/condensation reaction. First, an $R^1$-containing alcohol is de-protonated with sodium hydride (NaH) in DMF. The mesylated pyridine is then added and the mesyl-group is displaced by the $R^1$-containing alkoxide.

Alternative strategies to the reaction scheme illustrated in Scheme 1 can also be employed. For example, in Scheme 2, pyridine ether ligands may be synthesized through a condensation of the pyridine aldehyde with $R^3M$. Generally, $R^3M$ is a nucleophile such as an alkylating, arylating or hydrogenating reagent and M is a metal such as a main group metal, or a metalloid such as boron. The alkylating, arylating or hydrogenating reagent may be a Grignard, alkyl- or aryl-lithium or borohydride reagent. Further modification with another alkylating/arylating reagent as in step 2 provides pyridine ethers where $R^2$ is hydrogen while $R^1$ and $R^3$ are alkyl, aryl, or heteroaryl groups. An example of each type of pyridyl ether ligand synthesis is given in Examples 1, 2 and 3, respectively, below.

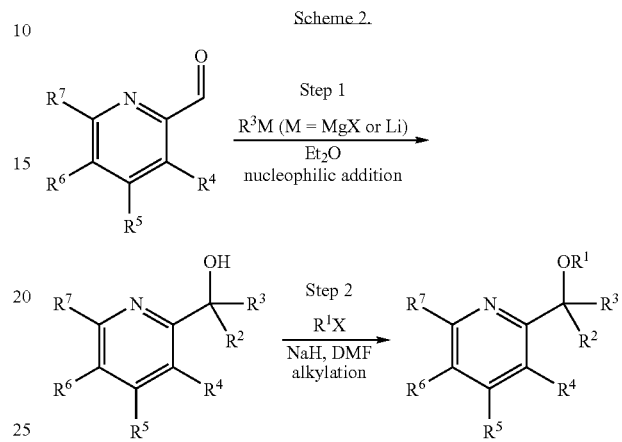

In a preferred embodiment, the ligand used in various embodiments of the present invention can be selected from the group consisting of the pyridyl-ether ligands shown below.

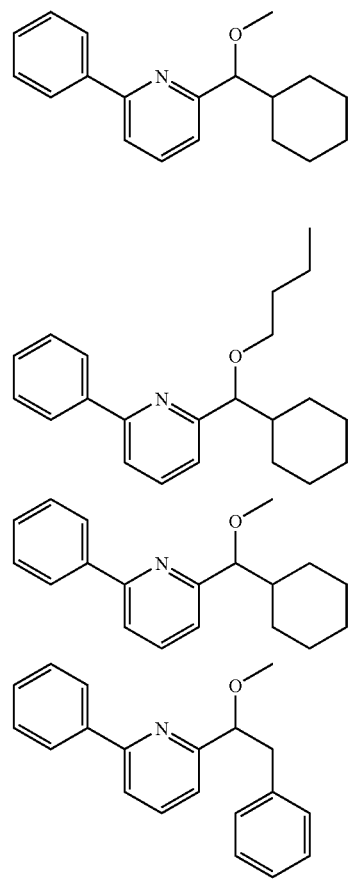

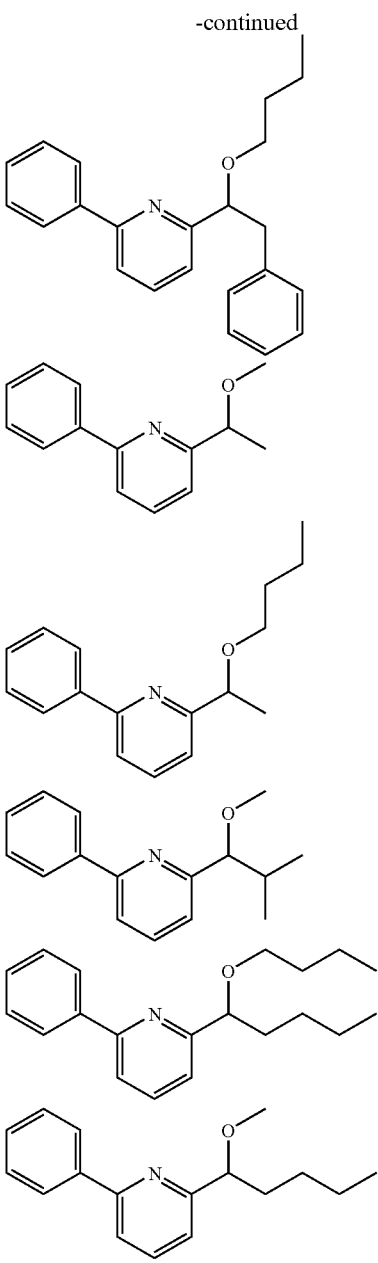

Once the desired ligand is formed, it can be combined with a Cr atom, ion, compound or other Cr precursor compound, and in some embodiments the present invention encompasses compositions that include any of the above-mentioned ligands in combination with an appropriate Cr precursor and an optional activator. For example, in some embodiments, the Cr precursor can be an activated Cr precursor, which refers to a Cr precursor (described below) that has been combined or reacted with an activator (described below) prior to combination or reaction with the ancillary ligand. As noted above, in one aspect the invention provides compositions that include such combinations of ligand and Cr atom, ion, compound or precursor. In some applications, the ligands are combined with a Cr compound or precursor and the product of such combination is not determined, if a product forms. For example, the ligand may be added to a reaction vessel at the same time as the Cr precursor compound along with the reactants, activators, scavengers, etc. Additionally, the ligand can be modified prior to addition to or after the addition of the Cr precursor, e.g., through a deprotonation reaction or some other modification.

The Cr metal precursor compounds may be characterized by the general formula $Cr(L)_n$ where L is an organic group, an inorganic group, or an anionic atom; and n is an integer of 1 to 6, and when n is not less than 2, L may be the same or different from each other. Each L is a ligand independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulfate, and combinations thereof. Optionally, two or more L groups are joined into a ring structure. One or more of the ligands L may be ionically bonded to Cr and, for example, L may be a non-coordinated or loosely coordinated or weakly coordinated anion (e.g., L may be selected from the group consisting of those anions described below in the conjunction with the activators). See Marks et al., Chem. Rev. 100, pp 1391-1434 (2000) for a detailed discussion of these weak interactions. The chromium precursors may be monomeric, dimeric or higher orders thereof.

Specific examples of suitable chromium precursors include, but are not limited to $(THF)_3CrMeCl_2$, $(Mes)_3Cr(THF)$ (Mes=mesityl=2,4,6-trimethylphenyl), $[\{TFA\}_2Cr(OEt_2)]_2$ (TFA=trifluoroacetate), $(THF)_3CrPh_3$, $CrCl_3(THF)_3$, $CrCl_4(NH_3)_2$, $Cr(NMe_3)_2Cl_3$, $CrCl_3$, $Cr(acac)_3$ (acac=acetylacetonato), $Cr(2\text{-ethylhexanoate})_3$, $Cr(neopentyl)_4$, $Cr(CH_2-C_6H_4-O-NMe_2)_3$, $Cr(TFA)_3$, $Cr(CH(SiMe_3)_2)_3$, $Cr(Mes)_2(THF)_3$, $Cr(Mes)_2(THF)$, $Cr(Mes)Cl(THF)_2$, $Cr(Mes)Cl(THF)_{0.5}$, $Cr(p\text{-tolyl})Cl_2(THF)_3$, $Cr(diisopropylamide)_3$, $Cr(picolinate)_3$, $[Cr_2Me_8][Li(THF)]_4$, $CrCl_2(THF)$, $Cr(NO_3)_3$, $[CrMe_6][Li(Et_2O)]_3$, $[CrPh_6][Li(THF)]_3$, $[CrPh_6][Li(n\text{-}Bu_2O)]_3$, $[Cr(C_4H_8)_3][Li(THF)]_3$, $CrCl_2$, $Cr(hexafluoroacetylacetonato)_3$, $(THF)_3Cr(\eta^2\text{-}2,2'\text{-Biphenyl})Br$ and mixtures thereof, and other well known chromium compounds commonly used as precursors in the formation of Cr complexes and catalysts.

The ligand may be mixed with a suitable metal precursor compound prior to or simultaneously with allowing the mixture to be contacted with the reactants (e.g., monomers). In this context, the ligand to metal precursor compound ratio can be in the range of about 0.1:1 to about 10:1, more specifically in the range of about 0.5:1 to about 2:1, and even more specifically about 1:1.

Generally, the ligand (or optionally a modified ligand as discussed above) is mixed with a suitable Cr precursor (and optionally other components, such an activator, or a reagent to exchange L groups on the chromium after contact between the chromium precursor and the ligand; e.g., Li(acac)) prior to or simultaneously with allowing the mixture to be contacted with the reactants (e.g., monomers). When the ligand is mixed with the Cr precursor compound, a Cr-ligand complex may be formed, which may itself be an active catalyst or may be transformed into a catalyst upon activation. In some embodiments the Cr precursor is contacted with other ligands, then activators, then monomers.

In some embodiments, the ligand will be mixed with a suitable metal precursor prior to or simultaneous with allowing the mixture to be contacted to the reactants. When the ligand is mixed with the metal precursor, a metal-ligand complex may be formed. In connection with the metal-ligand complex and depending on the ligand or ligands chosen, the metal-ligand complex may take the form of monomeric complexes, dimers, trimers or higher orders thereof or there may be two or more metal atoms that are bridged by one or more ligands. Furthermore, two or more ligands may coordinate to a single metal atom. The exact nature of the metal-ligand complex(es) formed depends on the chemistry of the ligand and the method of combining the metal precursor and ligand, such that a distribution of metal-ligand complexes may form with the number of ligands bound to the metal being greater than, equal to or less than the number of equivalents of ligands added relative to an equivalent of metal precursor. The ligand may, in some embodiments, be modified on binding to the metal, for example through a C—H activation reaction leading to a Cr-carbon bond, such as, for example, ortho-metallation of an arene moiety. Also, in some embodiments the ligand may be modified upon activation of the complex, for example through alkylation of a carbon of a C=N double bond & formation of a Cr—N covalent bond or reaction on the pyridine ring (for example, at positions $R_4$, $R_5$ or $R_6$). In further embodiments, a molecule of ethylene or another olefin (for example, 1-hexene) may insert into the aforementioned ortho-metallated arene.

Cr-ligand complexes can take a number of different coordination modes. General examples of possible coordination modes include those characterized by the following general formulas:

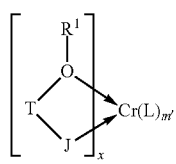

VI (a)

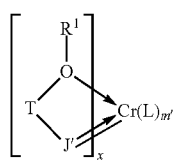

VI (b)

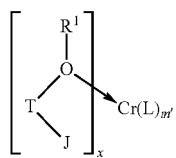

VI (c)

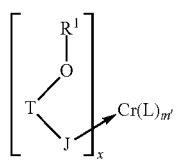

VI (d)

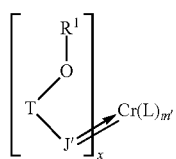

VI (e)

wherein $R^1$, L, and T are described above; x is 1 or 2; m' is 1, 2, 3, 4, or 5; and J represents the pyridine ring. J' represents the pyridine ring where the pyridine nitrogen is bonded to Cr through a dative bond, and another atom is bonded to the Cr through a covalent bond (e.g., orthometallation of the $R^7$ substituent). Numerous other coordination modes are possible, for example the ligands may bind to two chromium metal centers in a bridging fashion (see for example Cotton and Walton, *Multiple Bonds Between Metal Atoms* 1993, Oxford University Press). Some studies (for example, Rensburg et al., *Organometallics* 23, pp 1207-1222 (2004)) suggest that the ligand environment around Cr may be different at different points in the catalytic cycle. Hemilabile ligands, which can change their binding mode to the metal, may be useful in this regard.

In addition, the catalyst systems of this invention may be combined with other catalysts in a single reactor and/or employed in a series of reactors (parallel or serial).

The ligands-metal-precursors combinations and the metal ligand complexes, described above, are optionally activated in various ways to yield compositions active for selective ethylene oligomerization. For the purposes of this patent specification and appended claims, the terms "cocatalyst" and "activator" are used herein interchangeably and are defined to be any compound which can activate any one of the ligand-metal-precursor-combinations or the metal ligand complexes, described above by converting the combination, complex, or composition into a catalytically active species. Non-limiting activators, for example, include alumoxanes, aluminum alkyls, other metal or main group alkyl or aryl compounds, ionizing activators, which may be neutral or ionic, Lewis acids, reducing agents, oxidizing agents, and combinations thereof.

In one embodiment, alumoxane activators are utilized as an activator in the compositions useful in the invention. Alumoxanes are generally oligomeric compounds containing —Al($R^+$)—O— sub-units, where R is an alkyl group. Examples of alumoxanes include methylalumoxane (MAO), ethylalumoxane, isobutylalumoxane, and modified methylalumoxane (MMAO), which include alkyl groups other than methyl such as ethyl, isobutyl, and n-octyl, such as MMAO-3A, PMAO-IP (the latter referring to polymethylalumoxane-IP, manufactured by Akzo-Nobel and meaning an MAO prepared from a non-hydrolytic process). Alkylalumoxanes and modified alkylalumoxanes are suitable as catalyst activators, particularly when the abstractable ligand of the catalyst is a halide, alkoxide or amide. Mixtures of different alumoxanes and modified alumoxanes may also be used.

The activator compounds comprising Lewis-acid activators and in particular alumoxanes are specifically characterized by the following general formulae:

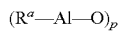

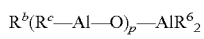

where $R^a$, $R^b$, $R^c$ and $R^e$ are, independently a $C_1$-$C_{30}$ alkyl radical, for example, methyl, ethyl, propyl, butyl, pentyl, hexyl, heptyl, octyl, nonyl, decyl, and "p" is an integer from 1 to about 50. Most specifically, $R^a$, $R^b$, $R^c$ and $R^d$ are each methyl and "p" is a least 4. When an alkyl aluminum halide or alkoxide is employed in the preparation of the alumoxane, one or more $R^a$, $R^b$, $R^c$ or $R^e$ are groups may be halide or alkoxide.

It is recognized that alumoxane is not a discrete material. An alumoxane is generally a mixture of both the linear and cyclic compounds. A typical alumoxane will contain free trisubstituted or trialkyl aluminum, bound trisubstituted or trialkyl aluminum, and alumoxane molecules of varying degree of oligomerization. For some embodiments, it is preferred that methylalumoxanes contain lower levels of trimethylaluminum. Lower levels of trimethylaluminum can be achieved by reaction of the trimethylaluminum with a Lewis base or by vacuum distillation of the trimethylaluminum or by any other means known in the art.

For further descriptions, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP0561476A1, EP0279586B1, EP0516476A1, EP0594218A1 and WO94/10180.

When the activator is an alumoxane (modified or unmodified), some embodiments select the maximum amount of activator at a 5000-fold molar excess Al/Cr over the catalyst precursor. The minimum preferred activator-to-catalyst-precursor is a 1:1 molar ratio. More specifically, the Al/Cr ratio is from 1000:1 to 100:1.

Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952, 540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP0561476A1, EP0279586B1, EP0594218A1 and EP0586665B1, and PCT publications WO94/10180 and WO99/15534, all of which are herein fully incorporated by reference. It may be preferable to use a visually clear methylalumoxane. A cloudy or gelled alumoxane can be filtered to produce a clear solution or clear alumoxane can be decanted from the cloudy solution. Another alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

Aluminum alkyl or organoaluminum compounds which may be utilized as activators (or scavengers) include trimethylaluminum, triethylaluminum, triisobutylaluminum, tri-n-hexylaluminum, tri-n-octylaluminum, diisobutylaluminum hydride, ethylaluminum dichloride, diethylaluminum chloride, diethylaluminum ethoxide and the like.

Ionizing Activators

In some embodiments, the activator includes compounds that may abstract a ligand making the metal complex cationic and providing a charge-balancing non-coordinating or weakly coordinating anion. The term "non-coordinating anion" (NCA) means an anion which either does not coordinate to said cation or which is only weakly coordinated to said cation thereby remaining sufficiently labile to be displaced by a Lewis base (for example, a neutral Lewis base).

It is within the scope of this invention to use an ionizing or stoichiometric activator, neutral or ionic, such as tri(n-butyl) ammonium tetrakis(pentafluorophenyl)boron, a tris(pentafluorophenyl)boron metalloid precursor or a tris(heptafluoronaphthyl)boron metalloid precursor, polyhalogenated heteroborane anions (WO98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include trisubstituted boron, tellurium, aluminum, gallium and indium or mixtures thereof. The three substituent groups are each independently selected from alkyls, alkenyls, halogen, substituted alkyls, aryls, arylhalides, alkoxy and halides. In some embodiments, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). In other embodiments, the three groups are alkyls having 1 to 4 carbon groups, phenyl, naphthyl or mixtures thereof. In further embodiments, the three groups are halogenated, specifically fluorinated, aryl groups. In even further embodiments, the neutral stoichiometric activator is tris(perfluorophenyl) boron or tris(perfluoronaphthyl) boron.

Ionic stoichiometric activator compounds may contain an active proton, or some other cation associated with, but not coordinated to, or only loosely coordinated to, the remaining ion of the ionizing compound. Such compounds and the like are described in European publications EP0570982A1, EP0520732A1, EP0495375A1, EP0500944B1, EP0277003A1 and EP0277004A1, and U.S. Pat. Nos. 5,153,157, 5,198,401, 5,066,741, 5,206,197, 5,241, 025, 5,384,299 and 5,502,124 and U.S. patent application Ser. No. 08/285,380, filed Aug. 3, 1994, all of which are herein fully incorporated by reference.

Ionic catalysts can be prepared by reacting a Cr compound with some neutral Lewis acids, such as $B(C_6F_6)_3$, which upon reaction with the abstractable ligand (X) of the Cr compound forms an anion, such as $([B(C_6F_5)_3(X)]^-)$, which stabilizes the cationic Cr species generated by the reaction. The catalysts can be prepared with activator components, which are ionic compounds or compositions.

In some embodiments, compounds useful as an activator component in the preparation of the ionic catalyst systems used in the process of this invention comprise a cation, which is optionally a Brönsted acid capable of donating a proton, and a compatible non-coordinating anion which is capable of stabilizing the active catalyst species which is formed when the two compounds are combined and said anion will be sufficiently labile to be displaced by olefinic substrates or other neutral Lewis bases such as ethers, nitriles and the like. Two classes of compatible non-coordinating anions useful herein have been disclosed in EP0277003A1 and EP0277004A1 published 1988: anionic coordination complexes comprising a plurality of lipophilic radicals covalently coordinated to and shielding a central charge-bearing metal or metalloid core; and, anions comprising a plurality of boron atoms such as carboranes, metallacarboranes and boranes.

In one preferred embodiment, the stoichiometric activators include a cation and an anion component, and may be represented by the following formula:

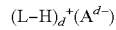

where L is a neutral Lewis base; H is hydrogen; $(L-H)^+$ is a Brönsted acid; $A^{d-}$ is a non-coordinating anion having the charge d-; and d is an integer from 1 to 3.

The cation component, $(L-H)_d^+$ may include Brönsted acids such as protons or protonated Lewis bases or reducible Lewis acids capable of protonating or abstracting a moiety, such as an alkyl or aryl, from the bulky ligand chromium catalyst precursor, resulting in a cationic transition metal species.

The activating cation $(L-H)_d^+$ may be a Brönsted acid, capable of donating a proton to the transition metal catalytic precursor resulting in a transition metal cation, including ammoniums, oxoniums, phosphoniums, silyliums, and mixtures thereof, specifically ammoniums of methylamine, aniline, dimethylamine, diethylamine, N-methylaniline, diphenylamine, trimethylamine, triethylamine, N,N-dimethylaniline, methyldiphenylamine, pyridine, p-bromo-N,N-dimethylaniline, p-nitro-N,N-dimethylaniline, phosphoniums from triethylphosphine, triphenylphosphine, and diphenylphosphine, oxoniums from ethers such as dimethyl ether diethyl ether, tetrahydrofuran and dioxane, sulfoniums from thioethers, such as diethyl thioethers and tetrahydrothiophene, and mixtures thereof. The activating cation $(L-H)_d^+$ may also be a moiety such as silver, tropylium, carbeniums, ferroceniums and mixtures, specifically carboniums and ferroceniums. In one embodiment $(L-H)_d^+$ can be triphenyl carbonium.

The anion component $A^{d-}$ includes those having the formula $[M^{k+}Q_n]^{d-}$ wherein k is an integer from 1 to 3; n is an integer from 2-6; n–k=d; M is an element selected from Group 13 of the Periodic Table of the Elements, specifically boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Specifically, each Q is a fluorinated hydrocarbyl group having 1 to 20 carbon atoms, more specifically each Q is a fluorinated aryl group, and most specifically each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst in the preparation of the improved catalysts of this invention are tri-substituted ammonium salts such as:

trimethylammonium tetraphenylborate, triethylammonium tetraphenylborate, tripropylammonium tetraphenylborate, tri(n-butyl)ammonium tetraphenylborate, tri(t-butyl) ammonium tetraphenylborate, N,N-dimethylanilinium tetraphenylborate, N,N-diethylanilinium tetraphenylborate, N,N-dimethyl-(2,4,6-trimethylanilinium) tetraphenylborate, tropillium tetraphenylborate, triphenylcarbenium tetraphenylborate, triphenylphosphonium tetraphenylborate, triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, trimethylammonium tetrakis-(2,3,4,6-tetrafluorophenyl) borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, trimethylammonium tetrakis (perfluoronaphthyl)borate, triethylammonium tetrakis (perfluoronaphthyl)borate, tripropylammonium tetrakis (perfluoronaphthyl)borate, tri(n-butyl)ammonium tetrakis (perfluoronaphthyl)borate, tri(t-butyl)ammonium tetrakis (perfluoronaphthyl)borate, N,N-dimethylanilinium tetrakis (perfluoronaphthyl)borate, N,N-diethylanilinium tetrakis (perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis (perfluoronaphthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(t-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis (perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri (n-butyl)ammonium tetrakis(3,5-bis(trifluoromethyl)phenyl)borate, tri(t-butyl)ammonium tetrakis(3,5-bis (trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis (trifluoromethyl)phenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, benzene(diazonium) tetrakis(3,5-bis(trifluoromethyl)phenyl)borate, and dialkyl ammonium salts such as: di-(1-propyl)ammonium tetrakis(pentafluorophenyl)borate, and dicyclohexylammonium tetrakis(pentafluorophenyl)borate; and additional tri-substituted phosphonium salts such as tri(o-tolyl)phosphonium tetrakis(pentafluorophenyl)borate, and tri(2,6-dimethylphenyl)phosphonium tetrakis (pentafluorophenyl)borate.

Most specifically, the ionic stoichiometric activator $(L-H)_d^+ (A^{d-})$ is N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis (trifluoromethyl)phenyl)borate, triphenylcarbenium tetrakis (perfluoronaphthyl)borate, triphenylcarbenium tetrakis (perfluorobiphenyl)borate, triphenylcarbenium tetrakis(3,5-bis(trifluoromethyl)phenyl)borate, or triphenylcarbenium tetra(perfluorophenyl)borate.

Other examples of preferred ionizing activators include, $HNMe(C_{18}H_{37})_2^+B(C_6F_5)_4^-$; $HNPh(C_{18}H_{37})_2^+B(C_6F_5)_4^-$ and $((4\text{-}n\text{-}Bu\text{-}C_6H_4)NH(n\text{-hexyl})_2)^+B(C_6F_5)_4^-$ and $((4\text{-}n\text{-}Bu\text{-}C_6H_4)NH(n\text{-decyl})_2)^+B(C_6F_5)_4^-$. Specific preferred $(L^{*-}H)^+$ cations are N,N-dialkylanilinium cations, such as $HNMe_2Ph^+$, substituted N,N-dialkylanilinium cations, such as $(4\text{-}n\text{-}Bu\text{-}C_6H_4)NH(n\text{-}C_6H_{13})_2^+$ and $(4\text{-}n\text{-}Bu\text{-}C_6H_4)NH(n\text{-}$ $C_{10}H_{21})_2^+$ and $HNMe(C_{18}H_{37})_2^+$. Specific examples of anions are tetrakis(3,5-bis(trifluoromethyl)phenyl)borate and tetrakis(pentafluorophenyl)borate.

In one embodiment, activation methods using ionizing ionic compounds not containing an active proton but capable of producing an active oligomerization catalyst are also contemplated. Such methods are described in relation to metallocene catalyst compounds in EP0426637A1, EP0573403A1 and U.S. Pat. No. 5,387,568, which are all herein incorporated by reference.

The process can also employ cocatalyst compounds or activator compounds that are initially neutral Lewis acids but form a cationic metal complex and a noncoordinating anion, or a zwitterionic complex upon reaction with the compounds of this invention. For example, tris(pentafluorophenyl) boron or aluminum may act to abstract a hydrocarbyl or hydride ligand to yield a cationic metal complex and stabilizing noncoordinating anion.

In some embodiments, ionizing activators may be employed as described in Köhn et al. (*J. Organomet. Chem.*, 683, pp 200-208, (2003)) to, for example, improve solubility.

In another embodiment, the aforementioned cocatalyst compounds can also react with the compounds to produce a neutral, uncharged catalyst capable of selective ethylene oligomerization. For example, Lewis acidic reagents such as, for example, alkyl or aryl aluminum or boron compounds, can abstract a Lewis basic ligand such as, for example, THF or Et$_2$O, from a compound yielding a coordinatively unsaturated catalyst capable of selective ethylene oligomerization.

When the cations of noncoordinating anion precursors are Brönsted acids such as protons or protonated Lewis bases (excluding water), or reducible Lewis acids such as ferrocenium or silver cations, or alkali or alkaline earth metal cations such as those of sodium, magnesium or lithium, the activator-to-catalyst-precursor molar ratio may be any ratio, however, useful ratios can be from 1000:1 to 1:1.

Combinations of two or more activators may also be used in the practice of this invention.

Another suitable ion forming, activating cocatalyst comprises a salt of a cationic oxidizing agent and a noncoordinating, compatible anion characterized by the general formula:

$$(OX^{e+})_d(A^{d-})_e$$

where $Ox^{e+}$ is a cationic oxidizing agent having a charge of e+; e is an integer from 1 to 3; d is an integer from 1 to 3, and $Ad^-$ is as previously defined. Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Brönsted acid containing activators, especially tetrakis(pentafluorophenyl)borate.

Group 13 Reagents, Divalent Metal Reagents, and Alkali Metal Reagents

Other general activators or compounds useful in an oligomerization reaction may be used. These compounds may be activators in some contexts, but may also serve other functions in the reaction system, such as alkylating a metal center or scavenging impurities. These compounds are within the general definition of "activator," but are not considered herein to be ion-forming activators. These compounds include a group 13 reagent that may be characterized by the formula $G^{13}R^{50}{}_{3-p}D_p$ where $G^{13}$ is selected from the group consisting of B, Al, Ga, In, and combinations thereof, p is 0, 1 or 2, each $R^{50}$ is independently selected from the group consisting of hydrogen, halogen, and optionally substituted alkyl, alkenyl, alkynyl, heteroalkyl, heteroalkenyl, heteroalkynyl, aryl, heteroaryl, and combinations thereof, and each D is independently selected from the group consisting of halogen, hydrogen, alkoxy, aryloxy, amino, mercapto, alkylthio, arylthio, phosphino and combinations thereof.

In other embodiments, the group 13 activator is an oligomeric or polymeric alumoxane compound, such as methylalumoxane and the known modifications thereof. See, for example, Barron, "*Alkylalumoxanes, Synthesis, Structure and Reactivity*", pp. 33-67 in *Metallocene-Based Polyolefins: Preparation, Properties and Technology*, J. Schiers and W. Kaminsky (eds.), Wiley Series in Polymer Science, John Wiley & Sons Ltd., Chichester, England, 2000, and references cited therein.

In other embodiments, a divalent metal reagent may be used that is characterized by the general formula $M'R^{50}{}_{2-p'}D_{p'}$ and p' is 0 or 1 in this embodiment and $R^{50}$ and D are as defined above. M' is the metal and is selected from the group consisting of Mg, Ca, Sr, Ba, Zn, Cd, Cu and combinations thereof.

In still other embodiments, an alkali metal reagent may be used that is defined by the general formula $M^{iV}R^{50}$ and in this embodiment $R^{50}$ is as defined above, and $M^{iV}$ is the alkali metal and is selected from the group consisting of Li, Na, K, Rb, Cs and combinations thereof. Additionally, hydrogen and/or silanes may be used in the catalytic composition or added to the polymerization system. Silanes may be characterized by the formula $SiR^{50}{}_{4-q}D_q$ where $R^{50}$ is defined as above, q is 1, 2, 3 or 4 and D is as defined above, with the proviso that at least one D is hydrogen.

Non-limiting examples of Group 13 reagents, divalent metal reagents, and alkali metal reagents useful as activators for the catalyst compounds described above include methyl lithium, butyl lithium, phenyl lithium, dihexylmercury, butylmagnesium, diethylcadmium, benzylpotassium, diethyl zinc, tri-n-butyl aluminum, diisobutyl ethylboron, diethylcadmium, di-n-butyl zinc and tri-n-amyl boron, and, in particular, the aluminum alkyls, such as trihexyl-aluminum, triethylaluminum, trimethylaluminum, and triisobutyl aluminum, diisobutyl aluminum bromide, diethylaluminum chloride, ethylaluminum dichloride, isobutyl boron dichloride, methyl magnesium chloride, ethyl beryllium chloride, ethyl calcium bromide, diisobutyl aluminum hydride, methyl cadmium hydride, diethyl boron hydride, hexylberyllium hydride, dipropylboron hydride, octylmagnesium hydride, butyl zinc hydride, dichloroboron hydride, di-bromo-aluminum hydride and bromocadmium hydride. Other Group 13 reagents, divalent metal reagents, and alkali metal reagents useful as activators for the catalyst compounds described above are known to those in the art, and a more complete discussion of these compounds may be found in U.S. Pat. Nos. 3,221,002 and 5,093,415, which are herein fully incorporated by reference.

Other activators include those described in PCT publication WO98/07515 such as tris(2,2',2"-nonafluorobiphenyl) fluoroaluminate, which publication is fully incorporated herein by reference. Combinations of activators are also contemplated by the invention, for example, alumoxanes and ionizing activators in combinations, see for example, EP0573120B1, PCT publications WO94/07928 and WO95/14044 and U.S. Pat. Nos. 5,153,157 and 5,453,410, all of which are herein fully incorporated by reference.

Other suitable activators are disclosed in WO98/09996, incorporated herein by reference, which describes activating bulky ligand metallocene catalyst compounds with perchlorates, periodates and iodates including their hydrates. WO98/30602 and WO98/30603, incorporated by reference, describe the use of lithium (2,2'-bisphenyl-ditrimethylsilicate).4THF as an activator for a bulky ligand metallocene catalyst compound. WO99/18135, incorporated herein by reference, describes the use of organo-boron-aluminum activators. EP0781299B1 describes using a silylium salt in combination with a non-coordinating compatible anion. Also, methods of activation such as using radiation (see EP0615981B1 herein incorporated by reference), electro-chemical oxidation, and the like are also contemplated as activating methods for the purposes of rendering the chromium complexes or compositions active for the selective oligomerization of olefins. Other activators or methods are described in for example, U.S. Pat. Nos. 5,849,852, 5,859,653 and 5,869,723 and WO98/32775, WO99/42467 (dioctadecylmethylammonium-bis(tris(pentafluorophenyl)borane) benzimidazolide), which are herein incorporated by reference.

Additional optional activators include metal salts of non-coordinating or weakly coordinating anions, for example where the metal is selected from Li, Na, K, Ag, Ti, Zn, Mg, Cs, and Ba.

It is within the scope of this invention that metal-ligand complexes and or ligand-metal-precursor-combinations can be combined with one or more activators or activation methods described above. For example, a combination of activators has been described in U.S. Pat. Nos. 5,153,157 and 5,453,410, EP0573120B1, and PCT publications WO94/07928 and WO95/14044. These documents all discuss the use of an alumoxane in combination with an ionizing activator.

In one embodiment, the molar ratio of metal (from the metal-ligand-complex or the ligand-metal-precursor-combination) to activator (specifically Cr: activator, specifically Cr: Al or Cr:B) can range from 1:1 to 1:5000. In another embodiment, the molar ratio of metal to activator employed can range from 1:1 to 1:500. In another embodiment, the molar ratio of metal to activator employed can range from 1:1 to 1:50. In another embodiment, the molar ratio of chromium to activator employed can range from 1:1 to 1:500. In another embodiment, the molar ratio of chromium to activator employed can range from 1:1 to 1:50.

In embodiments where more than one activator is used, the order in which the activators are combined with the metal-ligand-complex or the ligand-metal-precursor-combination may be varied.

In some embodiments, the process of the invention relates to the oligomerization, and more specifically the trimerization and/or tetramerization of ethylene. The ligand-metal-precursor-combinations, metal-ligand-complexes, and/or catalyst systems of this invention are particularly effective at oligomerizing and specifically trimerizing and/or tetramerizing ethylene to form 1-hexene and/or 1-octene.

In other embodiments, this invention relates to the oligomerization of α-olefins or co-oligomerization of ethylene with α-olefins. The trimerization of α-olefins is described in Köhn et al., *Angew. Chem. Int. Ed.,* 39 (23), pp 4337-4339 (2000).

Very generally, oligomerization can be carried out in the Ziegler-Natta or Kaminsky-Sinn methodology, including temperatures from −100° C. to 300° C. and pressures from atmospheric to 3000 atmospheres (303,900 kPa). Suspension, solution, slurry, gas phase, or high-pressure oligomerization processes may be employed with the catalysts and compounds of this invention. Such processes can be run in a batch, semi-batch, or continuous mode. Examples of such processes are well known in the art.

Suitable solvents for oligomerization are non-coordinating, inert liquids. Examples include straight and branched-chain hydrocarbons such as isobutane, butane, pentane, isopentane, hexane, isohexane, heptane, octane, dodecane, and mixtures thereof; cyclic and alicyclic hydrocarbons such as cyclohexane, cycloheptane, methylcyclohexane, methylcycloheptene, and mixtures thereof; perhalogenated hydrocarbons such as perfluorinated $C_{4-10}$ alkanes, chlorobenzene, and aromatic and alkylsubstituted aromatic compounds such as benzene, toluene, mesitylene, and xylene. Suitable solvents also include liquid olefins, which may act as monomers or comonomers including ethylene, propylene, 1-butene, 1-hexene, 1-pentene, 3-methyl-1-pentene, 4-methyl-1-pentene, 1-octene, and 1-decene. Additional suitable solvents include ionic liquids and supercritical fluids. Mixtures of the foregoing are also suitable.

Other additives that are useful in an oligomerization reaction may be employed, such as scavengers, promoters, modifiers, reducing agents, oxidizing agents, dihydrogen, aluminum alkyls, or silanes. For example, Jolly et al. (*Organometallics*, 16, pp 1511-1513 (1997)) has reported the use of magnesium as a reducing agent for Cr compounds that were synthesized as models for intermediates in selective ethylene oligomerization reactions.

In some useful embodiments, the activator (such as methylalumoxane or modified methylalumoxane-3A) is combined with the metal-ligand-complex or the ligand-metal-precursor-combination immediately prior to introduction into the reactor. Such mixing may be achieved by mixing in a separate tank then swift injection into the reactor, mixing in-line just prior to injection into the reactor, or the like. It has been observed that in some instances, a short activation time is very useful. Likewise, in-situ activation, where the catalyst system components are injected separately into the reactor, with or without monomer, and allowed to combine within the reactor directly is also useful in the practice of this invention. In some embodiments, the catalyst system components are allowed to contact each other for 30 minutes or less, prior to contact with monomer, alternately for 5 minutes or less, alternately for 3 minutes or less, alternately for 1 minute or less.

In another embodiment, the present invention relates to methods of producing oligomers of olefins, catalysts, ligands used to prepare the catalyst and catalyst compositions as described in the following paragraphs.

In a first embodiment, the present invention pertains to a composition comprising:

(1) a ligand characterized by the following general formula:

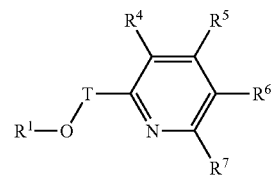

wherein $R^1$ is selected from the group consisting of optionally substituted hydrocarbyl and heteroatom containing hydrocarbyl;

T is a bridging group of the general formula -(T'$R^2R^3$)—, where T' is selected from the group consisting of carbon and silicon, $R^2$ and $R^3$ are independently selected from the group consisting of hydrogen, halogen, and optionally substituted hydrocarbyl, heteroatom containing hydrocarbyl, silyl, boryl, and combinations thereof, provided that $R^2$ and $R^3$ groups may be joined together to form one or more optionally substituted ring systems having from 3-50 non-hydrogen atoms;

$R^4$, $R^5$, $R^6$ and $R^7$ are independently selected from the group consisting of hydrogen, halogen, nitro, and optionally substituted hydrocarbyl and heteroatom containing hydrocarbyl, alkoxy, aryloxy, silyl, boryl, phosphino, amino, alkylthio, arylthio, and combinations thereof, and optionally two or more $R^1$, $R^2$, $R^3$, $R^4$, $R^5$, $R^6$ and $R^7$ groups may be joined to form one or more optionally substituted ring systems;

(2) a metal precursor compound characterized by the general formula $Cr(L)_n$ where each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, wherein two or more L groups may be combined in a ring structure having from 3 to 50 non-hydrogen atoms; n is 1, 2, 3, 4, 5, or 6; and (3) optionally, one or more activators.

2. The composition of paragraph 1, wherein $R^1$ through $R^7$ are selected from the group consisting of hydrogen, optionally substituted alkyl, heteroalkyl, aryl, heteroaryl, and combinations thereof, provided that $R^2$ and $R^3$ groups may be joined together to form one or more optionally substituted ring systems having from 3-50 non-hydrogen atoms and optionally two or more $R^1$, $R^2$, $R^3$, $R^4$, $R^5$, $R^6$ and $R^7$ groups may be joined to form one or more optionally substituted ring systems.

3. The composition of paragraph 1, wherein $R^1$ is selected from the group consisting of optionally substituted alkyl and aryl.

4. The composition of paragraph 1, wherein $R^7$ is selected from the group consisting of optionally substituted aryl and heteroaryl.

5. The composition of paragraph 1, wherein $R^7$ is optionally substituted phenyl.

6. The composition of paragraph 1, wherein $R^3$ is selected from the group consisting of optionally substituted alkyl, aryl and hydrogen.

7. The composition of paragraph 1, wherein $R^1$ is selected from the group consisting of optionally substituted alkyl, and aryl, $R^7$ is selected from the group consisting of optionally substituted aryl and heteroaryl and $R^3$ is selected from the group consisting of optionally substituted alkyl, aryl and hydrogen.

8. The composition of paragraph 1, wherein the ligand is selected from the group consisting of ligand A1 to A10.

9. A method of producing oligomers of olefins, comprising reacting an olefin with a catalyst under oligomerization conditions, wherein said oligomerization reaction has a selectivity of at least 70 mole percent for oligomer, and wherein said catalyst is said composition of any of claims 1 through 9.

10. The method of paragraph 9, wherein the activator is an alumoxane, which may optionally be used in any combination with group 13 reagents, divalent metal reagents, or alkali metal reagents.

11. The method of paragraph 9, wherein the activator is a neutral or ionic stoichiometric activator, which may optionally be used in any combination with group 13 reagents, divalent metal reagents, or alkali metal reagents.

12. The method of paragraph 9, wherein the activator is selected from the group consisting of modified methylaluminoxane (MMAO), methylaluminoxane (MAO), trimethylaluminum (TMA), triisobutyl aluminum (TIBA), diisobutylaluminumhydride (DIBAL), polymethylaluminoxane-IP (PMAO-IP), triphenylcarbonium tetrakis(perfluorophenyl)borate, N,N-dimethyl-anilinium tetrakis(perfluorophenyl)borate, N,N-di(n-decyl)-4-n-butyl-anilinium tetrakis(perfluorophenyl)borate, and mixtures thereof.

13. The method of paragraph 9, wherein the metal precursor is selected from the group consisting of $(THF)_3CrMeCl_2$, $(Mes)_3Cr(THF)$ (Mes=mesityl=2,4,6-trimethylphenyl), $[\{TFA\}_2Cr(OEt_2)]_2$ (TFA=trifluoroacetate), $(THF)_3CrPh_3$, $CrCl_3(THF)_3$, $CrCl_4(NH_3)_2$, $Cr(NMe_3)_2Cl_3$, $CrCl_3$, $Cr(acac)_3$ (acac=acetylacetonato), $Cr(2\text{-ethylhexanoate})_3$, $Cr(neopentyl)_4$, $Cr(CH_2—C_6H_4—O—NMe_2)_3$, $Cr(TFA)_3$, $Cr(CH(SiMe_3)_2)_3$, $Cr(Mes)_2(THF)_3$, $Cr(Mes)_2(THF)$, $Cr(Mes)Cl(THF)_2$, $Cr(Mes)Cl(THF)_{0.5}$, $Cr(p\text{-tolyl})Cl_2(THF)_3$, $Cr(diisopropylamide)_3$, $Cr(picolinate)_3$, $[Cr_2Me_8][Li(THF)]_4$, $CrCl_2(THF)$, $Cr(NO_3)_3$, $[CrMe_6][Li(Et_2O)]_3$, $[CrPh_6][Li(THF)]_3$, $[CrPh_6][Li(n\text{-}Bu_2O)]_3$, $[Cr(C_4H_8)_3][Li(THF)]_3$, $CrCl_2$, $Cr(hexafluoroacetylacetonato)_3$, $(THF)_3Cr(\eta^2\text{-}2,2'\text{-Biphenyl})Br$ and mixtures thereof.

14. The method of paragraph 9, wherein the metal precursor is selected from the group consisting of $(THF)_3CrMeCl_2$, $(THF)_3CrCl_3$, $(Mes)_3Cr(THF)$, $[\{TFA\}_2Cr(OEt_2)]_2$, $(THF)_3CrPh_3$, $(THF)_3Cr(\eta^2\text{-}2,2'\text{-Biphenyl})Br$ and mixtures thereof.

15. The method of any of paragraphs 9 through 14, wherein the olefin is a $C_2$ to $C_{12}$ olefin.

16. The method of any of paragraphs 9 through 14, wherein the olefin is a $C_2$ to $C_8$ olefin.

17. The method of any of paragraphs 9 through 14, wherein the olefin is ethylene.

18. The method of paragraph 17, wherein the process produces a trimer or tetramer of the olefin or mixture thereof.

19. The method of paragraph 17, wherein the process produces hexene.

20. The method of paragraph 17, wherein the process produces 1-hexene.

21. The method of paragraph 17, wherein the process produces octene.

22. The method of paragraph 17, wherein the process produces 1-octene.

23. The method of paragraph 17, wherein the process produces a mixture of hexene and octene.

24. The method of paragraph 17, wherein the process produces a mixture of 1-hexene and 1-octene.

25. The method of any of paragraphs 9 through 24, wherein the reaction occurs in a hydrocarbon solvent.

26. The method of any of paragraphs 9 through 24, wherein the reaction occurs in an aliphatic hydrocarbon solvent.

EXAMPLES

General: All air sensitive procedures were performed under a purified argon or nitrogen atmosphere in a Vacuum Atmospheres or MBraun glove box. All solvents used were anhydrous, de-oxygenated and purified according to known techniques (see for example, D. D. Perrin & W. L. F. Armarego *Purification of Laboratory Chemicals*, 3$^{rd}$ Ed., (Pergamon Press: New York, 1988)). All ligands and metal precursors were prepared according to procedures known to those of skill in the art, e.g., under inert atmosphere conditions, etc. Ethylene oligomerization experiments were carried out in a parallel batch reactor with in situ injection capability, as described in WO 04/060550, and U.S. Application No. 2004/0121448, each of which is incorporated herein by reference.

Quantitative analysis of the liquid olefin products was performed using an automated Agilent 6890 Dual Channel Gas Chromatograph fitted with 2 Flame Ionization Detectors. The liquid olefin products were first separated using RT-x1 columns (1.25 m length×0.25 mm thickness×1 μm width; manufactured by Restek and spooled into module by RVM Scientific) and quantified by flame ionization detection by comparison with calibration standards. Samples were loaded onto the columns from an 8×12 array of 1 mL glass vials using a CTC HTS PAL LC-MS autosampler purchased from LEAPTEC. Polyethylene yields were determined using a Bohdan model BA-100 automated weighing module.

Chromatography was performed on a Biotage Flash+chromatography system (Biotage AB, Uppsala, Sweden).

Ligand Synthesis

Synthesis of Pyridine Ethers as in Scheme 1

Example 1

Synthesis of Ligand A10

Step 1

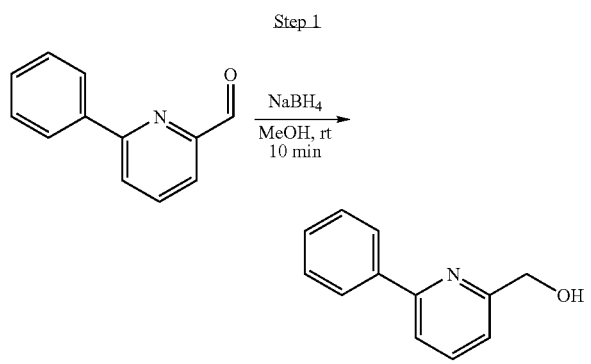

To a solution of 0.250 g (1.36 mmol) of 6-phenyl-2-pyridine aldehyde in 5 mL of methanol was added sodium borohydride (0.08 g, 2.05 mmol) portionwise with stirring under $N_2$ at ambient temperature. After 10 min, the reaction was quenched with 5 mL of saturated aqueous ammonium chloride solution. This solution was extracted with 3×50 mL EtOAc. The organic fractions were pooled, dried over $Na_2SO_4$. and concentrated. After removing the volatiles in vacuo, the resultant yellow oil was chromatographed on silica with 10% EtOAc/hexanes. Clean fractions were combined and the volatiles were removed to provide 0.250 g of 2-methylhydroxyl-6-phenyl pyridine as a clear oil (>99%).

Step 2

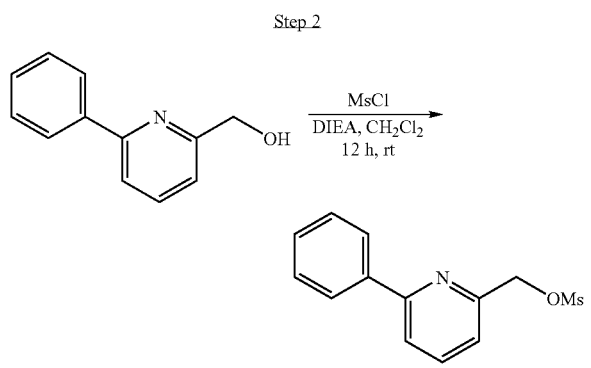

2-Methylhydroxyl-6-phenyl pyridine (0.26 g, 1.4 mmol) and DIEA (0.30 mL, 1.7 mmol) were dissolved in 8 mL of anhydrous methylene chloride. A 1 mL solution in methylene chloride of methanesulfonyl chloride (0.13 mL, 1.7 mmol) was added via syringe at ambient temperature. The mixture was vigorously stirred under $N_2$ for 12 h. The reaction was quenched with 5 mL MeOH and stirred for 10 min. The crude product was partitioned between water and methylene chloride, and extracted 3×10 mL methylene chloride. After removing the volatiles in vacuo, the resultant yellow oil was used immediately without further purification.

Step 3

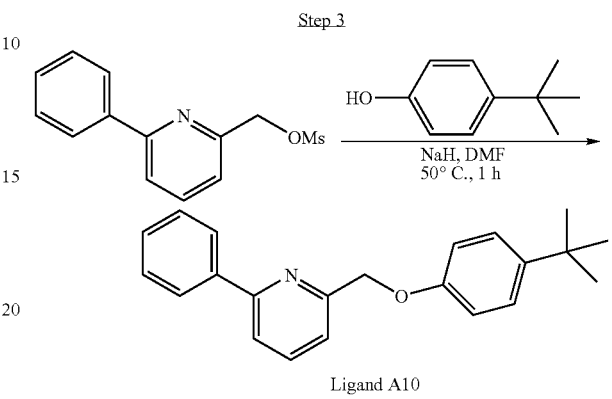

Ligand A10

To a solution of 30 g (0.2 mmol) of t-butylphenol in 2 mL of anhydrous DMF was added 5.0 mg (0.2 mmol) of sodium hydride at ambient temperature with vigorous stirring. After 1 h, a 1 mL DMF solution containing the pyridine mesylate (40 mg, 0.2 mmol) was added dropwise to the phenoxide. The resultant solution was heated at 50° C. for 1 h. After cooling, the crude material was concentrated in vacuo and purified via silica gel chromatography (20% EtOAc/Hexanes) to provide 50 mg of ligand A10 as a white solid (79%).

Alternative Syntheses of Pyridine Ethers as in Scheme 2

Example 2

General Synthesis of Alcohol Intermediate

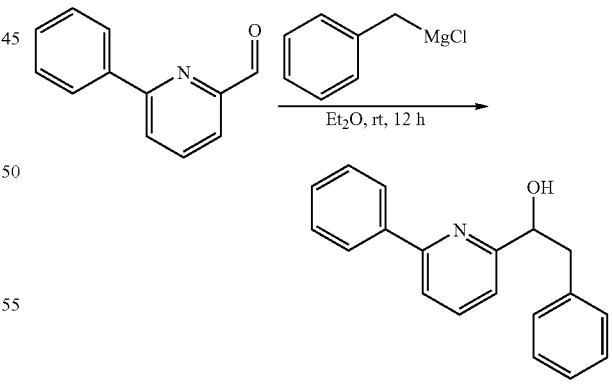

To a vigorously-stirred solution of 6-phenyl-2-pyridine aldehyde (0.50 g, 2.73 mmol) in 30 mL of anhydrous $Et_2O$ under $N_2$, was added a solution of benzylmagnesium chloride (3 mL of 1 M solution in $Et_2O$, 3.0 mmol) at ambient temperature. After 12 h, the reaction was quenched with 5 mL saturated aqueous ammonium chloride. This solution was extracted with 3×10 mL EtOAc. The organic fractions were pooled, dried over $Na_2SO_4$ and concentrated. After removing the volatiles in vacuo, the resultant yellow oil was chromatographed on silica with 10% EtOAc/hexanes. Clean fractions were combined and the volatiles were removed to provide 0.31 g of the alcohol intermediate as a yellow oil (41%).

Example 3

Synthesis of Ligand A8

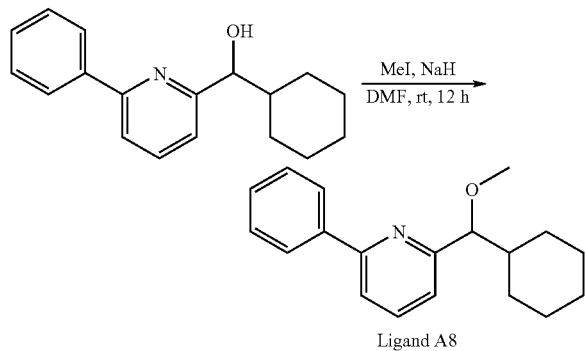

Ligand A8

Product Analysis.

After 1 hour of reaction, the parallel batch reactor was depressurized and the array was removed. The array of vials was then transferred to a room temperature aluminum block, and to each vial was added ca. 200 μL of toluene followed by 30-50 μL of water. The vials were stirred and then topped off with toluene to bring the total volume to ca. 800 μL. A Teflon sheet and rubber gasket were placed over the top of the array and an aluminum cover was screwed on the top to seal the array. The array was then mechanically agitated and centrifuged at 1500 rpm for 10 minutes before analyzing the composition of each well using Gas Chromatography with a Flame Ionization Detector (e.g. the GC-FID technique). Following the GC analysis of the array, the volatiles were removed under vacuum centrifuge and the vials were weighed in order to determine the yield of solid product. The calculated catalyst and cocatalyst residues were then subtracted from the weight to give the yield of non-volatile product (e.g., polyethylene) produced. Table 1 presents selected results from the selective ethylene oligomerization reactions performed in 96-well formats. In Table 1, 1-hexene selectivity is shown as a percentage and is defined as 100×[micromoles of 1-hexene]/[sum of micromoles of $C_6$-$C_{16}$ olefins].

TABLE 1

| Example | Ligand (0.3 μmol) | Chromium Precursor (0.3 μmol) | Method | Solvent | Reactor Temp (° C.) | Activation Method and mol Equivalents versus Cr | μmol Catalyst | μmol 1-Hexene Produced | Hexene Selectivity | mg Polyethylene Produced |
|---|---|---|---|---|---|---|---|---|---|---|
| 1 | A1 | $Cr(CH_3)Cl_2(THF)_3$ | 1 | Heptane | 50 | 200 MMAO-3A | 0.3 | 65 | >99 | 4 |
| 2 | A2 | $Cr(CH_3)Cl_2(THF)_3$ | 1 | Heptane | 50 | 200 MMAO-3A | 0.3 | 65 | 88 | 6 |
| 3 | A3 | $Cr(CH_3)Cl_2(THF)_3$ | 1 | Heptane | 50 | 200 MMAO-3A | 0.3 | 55 | 94 | 5 |
| 4 | A4 | $Cr(CH_3)Cl_2(THF)_3$ | 1 | Heptane | 50 | 200 MMAO-3A | 0.3 | 71 | 92 | 4 |
| 5 | A5 | $Cr(CH_3)Cl_2(THF)_3$ | 1 | Heptane | 50 | 200 MMAO-3A | 0.3 | 66 | 99 | 6 |
| 6 | A6 | $Cr(CH_3)Cl_2(THF)_3$ | 1 | Heptane | 50 | 200 MMAO-3A | 0.3 | 54 | 97 | 9 |
| 7 | A7 | $Cr(CH_3)Cl_2(THF)_3$ | 1 | Heptane | 50 | 200 MMAO-3A | 0.3 | 110 | >99 | 9 |
| 8 | A8 | $Cr(CH_3)Cl_2(THF)_3$ | 1 | Heptane | 50 | 200 MMAO-3A | 0.3 | 51 | >99 | 5 |
| 9 | A9 | $Cr(CH_3)Cl_2(THF)_3$ | 1 | Heptane | 50 | 200 MMAO-3A | 0.3 | 45 | 98 | 5 |
| 10 | A10 | $Cr(CH_3)Cl_2(THF)_3$ | 1 | Heptane | 50 | 200 MMAO-3A | 0.3 | 27 | 98 | 7 |

The 2-(cyclohexylmethanol)-6-phenyl-pyridine, prepared as in Example 2 and Scheme 2 step 1 above, (0.05 g, 0.2 mmol) was dissolved in 2.5 mL anhydrous DMF. To the vigorously-stirred solution was added NaH (0.005 g, 0.2 mmol), followed 5 min later by iodomethane (0.030 mL, 0.24 mmol). After 12 h, the crude product was concentrated and purified via silica gel chromatography (20% EtOAc/Hex) to yield 0.056 g of Ligand A8 as a clear oil (100%).

Method 1: Toluene 75° C. Temperature Complexation, Heptane Screening.

The ligand array (0.3 μmol of each ligand) was contacted with a toluene solution of the chromium complex (60 μL of a 5.0 mM solution, 0.3 μmol per well) and was stirred at 75° C. for a period of 1 hour (in the absence of ethylene). The array was then cooled to RT and the THF was removed by directing a stream of nitrogen or argon over each well in the array. Each well of the array was subsequently treated with 60 μL of n-Heptane and was stirred under 100-150 psi (0.69-1.03 MPa) of ethylene for 15 minutes. The array was then treated with a stock solution of the appropriate activator (200 μL per well, contact time of <5 minutes), and placed into the parallel batch reactor and stirred at 50° C. under 150 psi (1.03 MPa) of ethylene for 1 hour.

The results of selective ethylene trimerization or tetramerization using ligands of the invention in combination with chromium precursors or with isolated chromium metal complexes are surprising. The results illustrate that certain combinations are more productive in the trimerization of ethylene, for example, to produce 1-hexene at a higher selectivity and a lower selectivity toward polyethylene when compared with other chromium-ligand catalysts under similar conditions.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

The invention claimed is:
1. A composition comprising:
(1) a ligand characterized by the following general formula:

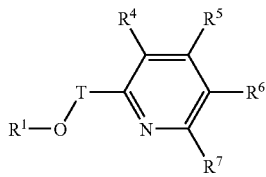

wherein R¹ is selected from the group consisting of optionally substituted alkyl;
T is a bridging group of the general formula -(T'R²R³)—, where T' is selected from the group consisting of carbon and silicon, R² and R³ are independently selected from the group consisting of hydrogen, optionally substituted hydrocarbyl;
R⁴, R⁵, and R⁶ are independently selected from the group consisting of hydrogen, optionally substituted hydrocarbyl;
R⁷ is phenyl or substituted phenyl;
(2) a metal precursor compound selected from the group consisting of (THF)₃CrMeCl₂, (Mes)₃Cr(THF), [{TFA}₂Cr(OEt₂)]₂, (THF)₃CrPh₃CrCl₃(THF)₃, CrCl₄(NH₃)₂, Cr(NMe₃)₂Cl₃, CrCl₃, Cr(acac)₃, Cr(2-ethylhexanoate)₃, Cr(neopentyl)₄, Cr(CH₂—C₆H₄-o-NMe₂)₃, Cr(TFA)₃, Cr(CH(SiMe₃)₂)₃, Cr(Mes)₂(THF)₃, Cr(Mes)₂(THF), Cr(Mes)Cl(THF)₂, Cr(Mes)Cl(THF)₀.₅, Cr(p-tolyl)Cl₂(THF)₃, Cr(diisopropylamide)₃, Cr(picolinate)₃, [Cr₂Me₈][Li(THF)]₄, CrCl₂(THF), Cr(NO₃)₃, [CrMe₆][Li(Et₂O)]₃, [CrPh₆][Li(THF)]₃, [CrPh₆][Li(n-Bu₂O)]₃, [Cr(C₄H₈)₃][Li(THF)]₃, CrCl₂, Cr(hexafluoroacetylacetonato)₃, (THF)₃ Cr(η²-2,2'-Biphenyl)Br and mixtures thereof, where Me=methyl, Et=ethyl, Bu=butyl, Ph=phenyl, THF=tetrahydrofuran, Mes=2,4,6-trimethylphenyl, TFA=trifluoroacetate, and acac=acetylacetonato; and
(3) optionally, one or more activators,
where the term substituted means a hydrogen is replaced with a group selected from the group consisting of hydroxy, alkoxy, alkylthio, phosphino, amino, halo, and silyl.

2. The composition of claim 1, wherein R⁷ is phenyl.

3. The composition of claim 1, wherein R³ is selected from the group consisting of alkyl, substituted alkyl, aryl, and hydrogen.

4. The composition of claim 1, wherein R¹ is selected from the group consisting of alkyl, substituted alkyl, and aryl, and R³ is selected from the group consisting of alkyl, substituted alkyl, aryl, and hydrogen.

5. A composition comprising:
(1) a ligand represented by the formulae

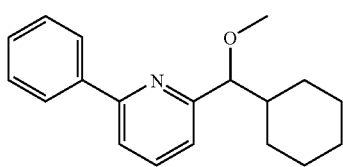

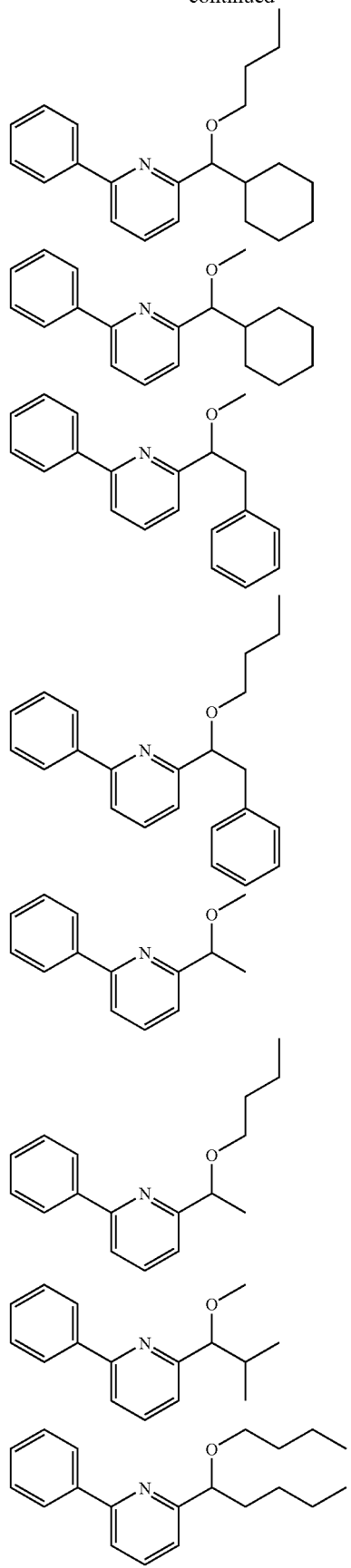

-continued

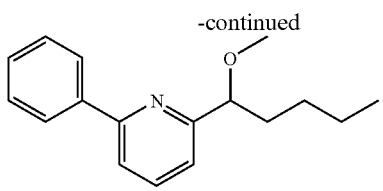

(2) a metal precursor selected from the group consisting of (THF)$_3$CrMeCl$_2$, (Mes)$_3$Cr(THF), [{TFA}$_2$Cr(OEt$_2$)]$_2$, (THF)$_3$CrPh$_3$, CrCl$_3$(THF)$_3$, CrCl$_4$(NH$_3$)$_2$, Cr(NMe$_3$)$_2$Cl$_3$, CrCl$_3$, Cr(acac)$_3$, Cr(2-ethylhexanoate)$_3$, Cr(neopentyl)$_4$, Cr(CH$_2$-C$_6$H$_4$-o-NMe$_2$)$_3$, Cr(TFA)$_3$, Cr(CH(SiMe$_3$)$_2$)$_3$, Cr(Mes)$_2$(THF)$_3$, Cr(Mes)$_2$(THF), Cr(Mes)Cl(THF)$_2$, Cr(Mes)Cl(THF)$_{0.5}$, Cr(p-tolyl)Cl$_2$(THF)$_3$, Cr(diisopropylamide)$_3$, Cr(picolinate)$_3$, [Cr$_2$Me$_8$][Li(THF)]$_4$, CrCl$_2$(THF), Cr(NO$_3$)$_3$, [CrMe$_6$][Li(Et$_2$O)]$_3$, [CrPh$_6$][Li(THF)]$_3$, [CrPh$_6$][Li(n-Bu$_2$O)]$_3$, [Cr(C$_4$H$_8$)$_3$][Li(THF)]$_3$, CrCl$_2$, Cr(hexafluoroacetylacetonato)$_3$, (THF)$_3$Cr($\eta^2$-2,2'-Biphenyl)Br and mixtures thereof, where Me=methyl, Et=ethyl, Bu=butyl, Ph=phenyl, THF=tetrahydrofuran, Mes=2,4,6-trimethylphenyl, TFA=trifluoroacetate, and acac=acetylacetonato; and (3) optionally, one or more activators.

6. A method of producing oligomers of olefins, comprising reacting an olefin with a catalyst under oligomerization conditions, wherein said oligomerization reaction has a selectivity of at least 70 mole percent for oligomer, and wherein said catalyst is said composition of claim 1.

7. The method of claim 6, wherein the activator is an alumoxane, which may optionally be used in any combination with group 13 reagents, divalent metal reagents, or alkali metal reagents.

8. The method of claim 6, wherein the activator is a neutral or ionic stoichiometric activator, which may optionally be used in any combination with group 13 reagents, divalent metal reagents, or alkali metal reagents.

9. The method of claim 6, wherein the activator is selected from the group consisting of modified methylaluminoxane, methylaluminoxane, trimethylaluminum, triisobutyl aluminum, diisobutylaluminumhydride, polymethylaluminoxane-IP, triphenylcarbonium tetrakis(perfluorophenyl)borate, N,N-dimethyl-anilinium tetrakis(perfluorophenyl)borate, N,N-di(n-decyl)-4-n-butyl-anilinium tetrakis(perfluorophenyl)borate, and mixtures thereof.

10. The method of claim 6, wherein the metal precursor is selected from the group consisting of (THF)$_3$CrMeCl$_2$, (Mes)$_3$ Cr(THF), [{TFA}$_2$Cr(OEt$_2$)]$_2$, (THF)$_3$CrPh$_3$, CrCl$_3$(THF)$_3$, CrCl$_4$(NH$_3$)$_2$, Cr(NMe$_3$)$_2$Cl$_3$, CrCl$_3$, Cr(acac)$_3$, Cr(2-ethylhexanoate)$_3$, Cr(neopentyl)$_4$, Cr(CH$_2$-C$_6$H$_4$-o-NMe$_2$)$_3$, Cr(TFA)$_3$, Cr(CH(SiMe$_3$)$_2$)$_3$, Cr(Mes)$_2$(THF)$_3$, Cr(Mes)$_2$(THF), Cr(Mes)Cl(THF)$_2$, Cr(Mes)Cl(THF)$_{0.5}$, Cr(p-tolyl)Cl$_2$(THF)$_3$, Cr(diisopropylamide)$_3$, Cr(picolinate)$_3$, [Cr$_2$Me$_8$][Li(THF)]$_4$, CrCl$_2$(THF), Cr(NO$_3$)$_3$, [CrMe$_6$][Li(Et$_2$O)]$_3$, [CrPh$_6$][Li(THF)]$_3$, [CrPh$_6$][Li(n-Bu$_2$O)]$_3$, [Cr(C$_4$H$_8$)$_3$][Li(THF)]$_3$, CrCl$_2$, Cr(hexafluoroacetylacetonato)$_3$, (THF)$_3$Cr($\eta^2$-2,2'-Biphenyl)Br and mixtures thereof, where Me=methyl, Et=ethyl, Bu=butyl, Ph=phenyl, THF=tetrahydrofuran, Mes=2,4,6-trimethylphenyl, TFA=trifluoroacetate, and acac=acetylacetonato.

11. The method of claim 6, wherein the metal precursor is selected from the group consisting of (THF)$_3$CrMeCl$_2$, (THF)$_3$CrCl$_3$, (Mes)$_3$Cr(THF), [{TFA}$_2$Cr(OEt$_2$)]$_2$, (THF)$_3$CrPh$_3$, (THF)$_3$Cr($\eta^2$-2,2'-Biphenyl)Br and mixtures thereof, where Me=methyl, Et=ethyl, Ph=phenyl, THF=tetrahydrofuran, Mes=2,4,6-trimethylphenyl, and TFA=trifluoroacetate.

12. The method of any of claim 6, wherein the olefin is a C$_2$ to C$_{12}$ olefin.

13. The method of claim 6, wherein the olefin is a C$_2$ to C$_8$ olefin.

14. The method of claim 6, wherein the olefin is ethylene.

15. The method of claim 14, wherein the process produces a trimer or tetramer of the olefin or mixture thereof.

16. The method of claim 14, wherein the process produces hexene.

17. The method of claim 14, wherein the process produces 1-hexene.

18. The method of claim 14, wherein the process produces octene.

19. The method of claim 14, wherein the process produces 1-octene.

20. The method of claim 14, wherein the process produces a mixture of hexene and octene.

21. The method of claim 14, wherein the process produces a mixture of 1-hexene and 1-octene.

22. The method of claim 6 wherein the reaction occurs in a hydrocarbon solvent.

23. The composition of claim 1, wherein the metal precursor is selected from the group consisting of (THF)$_3$CrMeCl$_2$, (THF)$_3$CrCl$_3$, (Mes)$_3$Cr(THF), [{TFA}$_2$Cr(OEt$_2$)]$_2$, (THF)$_3$CrPh$_3$, (THF)$_3$Cr($\eta^2$-2,2'-Biphenyl)Br and mixtures thereof, where Me=methyl, Et=ethyl, Ph=phenyl, THF=tetrahydrofuran, Mes=2,4,6-trimethylphenyl, and TFA=trifluoroacetate.

24. The composition of claim 1, wherein the composition comprises an activator and the activator is selected from the group consisting of modified methylaluminoxane, methylaluminoxane, trimethylaluminum triisobutyl aluminum, diisobutylaluminumhydride, polymethylaluminoxane-IP, triphenylcarbonium tetrakis(perfluorophenyl)borate, N,N-dimethyl-anilinium tetrakis(perfluorophenyl)borate, N,N-di(n-decyl)-4-n-butyl-anilinium tetrakis(perfluorophenyl)borate, and mixtures thereof.

25. The composition of claim 1, wherein R$^1$ is alkyl or aryl.

26. A composition comprising:

(1) a ligand characterized by the following general formula:

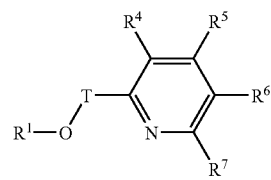

wherein R$^1$ is selected from the group consisting of alkyl, aryl, hydroxy, alkoxy, alkylthio, phosphino, amino, halo, and silyl;

T is a bridging group of the general formula -(T'R$^2$R$^3$)—, where T' is selected from the group consisting of carbon and silicon, R$^2$ and R$^3$ are independently selected from the group consisting of hydrogen, optionally substituted hydrocarbyl;

$R^4$, $R^5$, and $R^6$ are independently selected from the group consisting of hydrogen, optionally substituted hydrocarbyl;

$R^7$ is phenyl or substituted phenyl;

(2) a metal precursor compound selected from the group consisting of $(THF)_3CrMeCl_2$, $(Mes)_3Cr(THF)$, $[\{TFA\}_2Cr(OEt_2)]_2$, $(THF)_3CrPh_3$, $CrCl_3(THF)_3$, $CrCl_4(NH_3)_2$, $Cr(NMe_3)_2Cl_3$, $CrCl_3$, $Cr(acac)_3$, $Cr(2\text{-ethylhexanoate})_3$, $Cr(neopentyl)_4$, $Cr(CH_2\text{-}C_6H_4\text{-}o\text{-}NMe_2)_3$, $Cr(TFA)_3$, $Cr(CH(SiMe_3)_2)_3$, $Cr(Mes)_2(THF)_3$, $Cr(Mes)_2(THF)$, $Cr(Mes)Cl(THF)_2$, $Cr(Mes)Cl(THF)_{0.5}$, $Cr(p\text{-tolyl})Cl_2(THF)_3$, $Cr(diisopropylamide)_3$, $Cr(picolinate)_3$, $[Cr_2Me_8][Li(THF)]_4$, $CrCl_2(THF)$, $Cr(NO_3)_3$, $[CrMe_6][Li(Et_2O)]_3$, $[CrPh_6][Li(THF)]_3$, $[CrPh_6][Li(n\text{-}Bu_2O)]_3$, $[Cr(C_4H_8)_3][Li(THF)]_3$, $CrCl_2$, $Cr(hexafluoroacetylacetonato)_3$, $(THF)_3Cr(\eta^2\text{-}2,2'\text{-Biphenyl})Br$ and mixtures thereof, where Me=methyl, Et=ethyl, Bu=butyl, Ph=phenyl, THF=tetrahydrofuran, Mes=2,4,6-trimethylphenyl, TFA=trifluoroacetate, and acac=acetylacetonato; and (3) optionally, one or more activators, where the term substituted means a hydrogen is replaced with a group selected from the group consisting of hydroxy, alkoxy, alkylthio, phosphino, amino, halo, and silyl.

27. The composition of claim 26, wherein $R^1$ is selected from the group consisting of hydroxy, alkoxy, alkylthio, phosphino, amino, halo, and silyl.

* * * * *